US010874725B2

(12) United States Patent
Henco et al.

(10) Patent No.: US 10,874,725 B2
(45) Date of Patent: *Dec. 29, 2020

(54) METHOD OF PROVIDING PATIENT SPECIFIC IMMUNE RESPONSE IN AMYLOIDOSES AND PROTEIN AGGREGATION DISORDERS

(71) Applicant: New York University, New York, NY (US)

(72) Inventors: Karsten Henco, Düsseldorf (DE); Roger Nitsch, Zumikon (CH); Jan Grimm, Dübendorf (CH); Anja Zeller, Zürich (CH); Marcel Maier, Zürich (CH)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/845,110

(22) Filed: Dec. 18, 2017

(65) Prior Publication Data

US 2018/0110845 A1    Apr. 26, 2018

Related U.S. Application Data

(63) Continuation of application No. 15/177,980, filed on Jun. 9, 2016, now abandoned, which is a continuation of application No. 12/733,437, filed as application No. PCT/EP2008/007127 on Sep. 1, 2008, now Pat. No. 9,370,531.

(60) Provisional application No. 60/967,178, filed on Aug. 31, 2007.

(30) Foreign Application Priority Data

Aug. 31, 2007 (EP) .................................... 07017135

(51) Int. Cl.
| | | |
|---|---|---|
| *A61K 39/00* | (2006.01) | |
| *A61K 39/39* | (2006.01) | |
| *A61K 31/7088* | (2006.01) | |
| *C12N 15/117* | (2010.01) | |
| *A61P 25/28* | (2006.01) | |
| *G01N 33/68* | (2006.01) | |

(52) U.S. Cl.
CPC ...... *A61K 39/0007* (2013.01); *A61K 31/7088* (2013.01); *A61K 39/39* (2013.01); *G01N 33/6896* (2013.01); *A61K 2039/53* (2013.01); *A61K 2039/545* (2013.01); *A61K 2039/55511* (2013.01); *A61K 2039/55561* (2013.01); *A61K 2039/57* (2013.01); *A61K 2039/575* (2013.01); *A61P 25/28* (2018.01); *C12N 15/117* (2013.01); *G01N 2333/4709* (2013.01); *Y02A 50/30* (2018.01)

(58) Field of Classification Search
CPC ............... A61K 31/7088; A61K 39/39; A61K 2039/53; A61K 2039/55511; A61K 2039/55561; A61K 2039/57; A61K 2039/575; A61P 25/28; C12N 15/117
See application file for complete search history.

(56) References Cited

U.S. PATENT DOCUMENTS

| | | |
|---|---|---|
| 6,194,388 B1 | 2/2001 | Krieg et al. |
| 6,339,068 B1 | 1/2002 | Krieg et al. |
| 6,544,518 B1 | 4/2003 | Friede et al. |
| 9,370,531 B2 | 6/2016 | Henco et al. |
| 10,383,887 B2 | 8/2019 | Wisniewski et al. |
| 2004/0198680 A1 | 10/2004 | Krieg |
| 2006/0040887 A1 | 2/2006 | Karaolis |
| 2006/0159693 A1 | 7/2006 | Ward |
| 2006/0229233 A1 | 10/2006 | Frenkel et al. |
| 2006/0280733 A1 | 12/2006 | Kayed et al. |
| 2007/0224210 A1 | 9/2007 | Krieg et al. |
| 2008/0009455 A9 | 1/2008 | Krieg et al. |
| 2010/0272785 A1* | 10/2010 | Jurk ........................ A61P 31/00 424/450 |
| 2011/0060035 A1 | 3/2011 | Wisniewski et al. |
| 2019/0328764 A1 | 10/2019 | Wisniewski et al. |

FOREIGN PATENT DOCUMENTS

| | | |
|---|---|---|
| DE | 102005020798 A1 | 11/2006 |
| WO | WO 2000/062800 A2 | 10/2000 |
| WO | WO 01/53457 A2 | 7/2001 |
| WO | WO 03054161 A2 | 7/2003 |
| WO | 2004/0007743 A2 | 1/2004 |
| WO | WO 2006/134423 A2 | 12/2006 |

(Continued)

OTHER PUBLICATIONS

Mutwiri G et al. Biological activity of immunostimulatory CpG DNA motifs in domestic animals. Vet. Immunol. Immunopathol. 91, 89-103. (Year: 2003).*
Klinman DM et al. Repeated administration of synthetic oligodeoxynucleotides expressing CpG motifs provides long-term protection against bacterial infection. Infection & Immunity, 67(11), 5658-5663. (Year: 1999).*
Definition for "subclinical", retrieved from Wiktionary (en.wiktionary.org/w/index.php?title=subclinical&oldid=51386311) on Jan. 6, 2020. (Year: 2020).*
Baines J et al. Immune-mediated tumor regression induced by CpG-containing oligodeoxynucleotides. Clin. Cancer Res. 2003, 9, 2693-2700. (Year: 2003).*

(Continued)

*Primary Examiner* — Kimberly Ballard
(74) *Attorney, Agent, or Firm* — Troutman Pepper Hamilton Sanders LLP (Rochester)

(57) ABSTRACT

A treatment of Alzheimer's disease and other disorders involving protein misfolding or aggregation is provided by enhancing or sustaining an antibody response against predominantly directed against pathological protein aggregates or neo-epitopes present on pathogenic forms of said protein or protein complex. Furthermore, therapeutic methods are described, wherein ex vivo stimulated antigen-selected peripheral blood lymphocytes are regrafted into the cognate donor.

19 Claims, 6 Drawing Sheets

(56) References Cited

FOREIGN PATENT DOCUMENTS

| WO | WO 2007/030580 A2 | 3/2007 |
|---|---|---|
| WO | WO 2009/027105 A2 | 3/2009 |
| WO | WO 2009/105641 A2 | 8/2009 |

OTHER PUBLICATIONS

Kielian T. Toll-like receptors in central nervous system glial inflammation and homeostasis. J. Neurosci. Res. 2006, 83(5), 711-730. (Year: 2006).*
Shen Y et al. CpG oligodeoxynucleotides prevent the development of scleroderma-like syndrome in tight-skin mice by stimulating a Th1 immune response. J. Invest. Dermatol, 2005, 124, 1141-1148. (Year: 2005).*
Tahara K et al. Role of toll-like receptor signaling in Abeta uptake and clearance. Brain, 2006, 129, 3006-3019. (Year: 2006).*
Von Beust BR et al. Improving the therapeutic index of CpG oligodeoxynucleotides by intralymphatic administration. Eur. J. Immunol. 2005, 35, 1869-1876. (Year: 2005).*
International Search Report for International Patent Application No. PCT/US2009/034677 (dated Sep. 17, 2009).
Lotz et al. "Amyloid Beta Peptide 1-40 Enhances the Action of Toll-Like Receptor-2 and -4 Agonists but Antagonizes Toll-Like Receptor-9-Induced Inflammation in Primary Mouse Microglial Cell Cultures," Journal of Neurochemistry 94(2):289-98 (2005).
McCluskie et al. "Enhancement of Infectious Disease Vaccines Through TLR9-Dependent Recognition of CpG DNA," Current Topics in Microbiology and Immunology 311:155-78 (2006) (abstract).
Sethi et al. "Postexposure Prophylaxis Against Prion Disease with a Stimulator of Innate Immunity," The Lancet 360(9328):229-30 (2002) (abstract).
Tahara et al. "Role of Toll-like Receptor Signaling in Amyloid Beta-protein Uptake and Clearance," Brain 129:3006-3019 (2006).
Crack et al. "Toll-like Receptors in the Brain and Their Potential Roles in Neuropathology," Immunology and Cell Biology 85:476-480 (2007).
Kreig, Arthur M. "Therapeutic Potential of Toll-like Receptor 9 Activation," Nature Reviews 5:471-484 (2006).
Agrawal et al. "Synthetic Agonists of Toll-like Receptors 7, 8 and 9," Biochemical Society Transactions 35(6):1461-1467 (2007).
Sugiyama et al. "CpG RNA: Identification of Novel Single-Stranded RNA That Stimulates Human CD14+CD11c+ Monocytes," The Journal of Immunology 174:2273-2279 (2005).
Written Opinion of the International Searching Authority for International Patent Application No. PCT/US2009/034677 (dated Sep. 17, 2007).
Heikenwalder et al., "Lymphoid Follicle Destruction and Immunosuppression After Repeated CpG Oligodeoxynucleotide Administration," Nat. Med. 10:187-192 (2004).
Fiala et al., "Ineffective Phagocytosis of Amyloid-beta by Macrophages of Alzheimer's Disease Patients," J. Alzheimers Dis. 7:221-232 (2005).
Qiao et al., "Neuroinflammation-Induced Acceleration of Amyloid Deposition in the APPV717F Transgenic Mouse," Eur. J. Neurosci. 14:474-482 (2001).
Sheng et al., "Lipopolysaccharide-Induced-Neuroinflammation Increases Intracellular Accumulation of Amyloid Precursor Protein and Amyloid β Peptide in APPswe Transgenic Mice," Neurobiol. Disease 14:133-145 (2003).
Lee et al., "LPS-Induced Inflammation Exacerbates Phospho Tau Pathology in rTg4510.Mice," J. Neuroinflammation 7:56 (2010).
Bhaskar et al., "Regulation of Tau Pathology by the Microglial Fractalkine Receptor," Neuron 68(1): 19-31 (2010).
Tauber et al., "Stimulation of Toll-like Receptor 9 by Chronic Intraventricular Unmethylated Cytosine-Guanine DNA Infusion Causes Neuroinflammation and Impaired Spatial Memory," J. Neuropathol. Exp. Neurol. 68:1116 (2009).
Capolunghi et al., "Pharmacological Inhibition of TLR9 Activation Blocks Autoantibody Production in Human B cells from SLE Patients," Rheumatology 49(12):2281-9 (2010).
Guerrier et al., "TLR9 Drives the Development of Transitional B Cells Towards the Marginal Zone Pathway and Promotes Autoimmunity," J Autoimmun 39(3):173-9 (2012).
Azulay-Debby et al., "CpG DNA Stimulates Autoreactive Immature B cells in the Bone Marrow," Eur J Immunol. 37(6):1463-75 (2007).
Pfeifer et al., "Cerebral Hemorrhage After Passive anti-Aβ Immunotherapy," Science 298:1379 (2002).
Wilcock et al, "Passive Immunotherapy Against Abeta in Aged APP-Transgenic Mice Reverses Cognitive Deficits and Depletes Parenchymal Amyloid Deposits in Spite of Increased Vascular Amyloid and Microhemorrhage," J Neuroinflammation 1:24 (2004).
Racke et al., "Exacerbation of Cerebral Amyloid Angiopathy-Associated Microhemorrhage in Amyloid Precursor Protein Transgenic Mice by Immunotherapy is Dependent on Antibody Recognition of Deposited Forms of Amyloid beta," J Neurosci 25:629-36 (2005).
Wilcock et al., "Amyloid-beta Vaccination, but not Nitro-Nonsteriodal Anti-Inflammatory Drug Treatment, Increases Vascular Amyloid and Microhemorrhage while both Reduce Parenchymal Amyloid," Neuroscience 144:950-960 (2007).
Nelson et al., "Correlation of Alzheimer's Disease Neuropathologic Changes and Cognitive Status: a Review of the Literature," Journal of Neuropathology and Experimental Neurology 71(5):362-381 (2012).
Will R., "Acquired Prion Disease: Iatrogenic CJD, Variant CJD, Kuru," British Medical Bulletin 66:255-65 (2003).
Lee et al., "Abeta42 Immunization in Alzheimer's Disease Generates Abeta N-terminal Antibodies," Ann. Neurol. 58(3): 430-435 (2005).
Examination Report for corresponding European Patent Application No. 08785778.5 (dated Jun. 11, 2014).
Scholtzova, H. et al., "Induction of Toll-Like Receptor 9 Signaling as a Method for Ameliorating Alzheimer's Disease-Related Pathology," J. Neuro. 29(6):1846-54 (2009).
Vollmer et al., "Immunotherapeutic Applications of CpG Oligonucleotide TLR9 Agonists," Adv Drug Deliv Rev. 61(3):195-204 (2009).
Hartman et al., "Delineation of a CpG Phosphorothioate Oligodeoxynucleotide for Activating Primate Immune Responses In Vitro and In Vivo," J Immunol. 164(3): 1617-24 (2000).
Scheiermann et al., "Clinical Evaluation of CpG Oligonucleotides as Adjuvants for Vaccines Targeting Infectious Diseases and Cancer," Vaccine 32: 6377-6389 (2014).
Amendment for U.S. Appl. No. 12/918,739 dated Jan. 4, 2016.
Armstrong et al., "What Determines the Molecular Composition of Abnormal Protein Aggregates in Neurodegenerative Disease?" Neuropathol. 28:351-365 (2008).
Klinman DM., "Immunotherapeutic Uses of CpG Oligodeoxynucleotides," Nat. Rev. Immunol. 4:1-10 (2004).
Vasilakos, et al., "Adjuvant activities of immune response modifier R-848: comparison with CpG ODN," Cellular Immunology 204:64-74 (2000).
Wang et al., "Site-specific UBITh® amyloid-β vaccine for immunotherapy of Alzheimer's disease," Vaccine 25:3041-3052 (2007).
Written Opinion of the International Searching Authority for International Application No. PCT/EP2008/007127 (dated Dec. 18, 2008).
International Preliminary Report on Patentability for International Application No. PCT/EP2008/007127 (dated Mar. 2, 2010).
Spinner et al., "CpG oligodeoxynucleotide-enhanced humoral immune response and production of antibodies to prion protein PrPsc in mice immunized with 139A scrapie-associated fibrils," Journal of Leukocyte Biology 81:1374-1385(2007).
Scholtzova, H. et al., "Stimulation of innate immunity with the TLR9 Agonist CpG is beneficial in AD model mice," Abstract of presentation given at Neuroscience Aug. 17, 2007, San Diego, CA.
International Search Report for International Application No. PCT/EP2008/007127 (dated Mar. 4, 2009).

(56) References Cited

OTHER PUBLICATIONS

Lan Tao et al., "Stabilized immune modulatory RNA compounds as agonists of Toll-like Receptors 7 and 8," Proceedings of the National Academy of Sciences of the United States of America 104(34):13750-13755 (2007).
Iribarren et al., "CpG-containing oligodeoxynucleotide promotes microgliai cell uptake of amyloid beta 1-42 peptide by up-regulating the expression of the G-protein-coupled receptor mFPR2," FASEB Journal 19(14):2032-34 (2005).
Examination Report for EP08785778.5 dated Jul. 22, 2016.
Sethi et al., "Postexposure Prophylaxis Against Prion Disease with a Stimulator of Innate Immunity," Lancet 360(9328):229-30 (2002).
Hampel et al., "The Future of Alzheimer's Disease: The Next 10 years," Progress Neurobiol. 95:718-728 (2011).
Lemere et al., "Amyloid-beta Immunotherapy for the Prevention and Treatment of Alzheimer's Disease: Lessons From Mice, Monkeys, and Humans," Rejuvenation Res. 9(1):77-84 (2006).
Liu et al., "Amyloid-beta Peptide Alters Intracellular Vesicle Trafficking and Cholesterol Homeostasis," Proc Natl Acad Sci USA 95:13266-13271 (1998).
Masliah et al., "Amyloid Protein Precursor Stimulates Excitatory Amino Acid Transport," J. Biol. Chem. 273(20):12548-12554 (1998).
Perez et al., "The Beta-amyloid Precursor Protein of Alzheimer's Disease Enhances Neuron Viability and Modulates Neuronal Polarity," J. Neurosci. 17:9407-9414 (1997).
Plant et al., "The Production of Amyloid Beta Peptide is a Critical Requirement for the Viability of Central Neurons," J. Neurosci. 23:5531-5535 (2003).
Small DH, "The Role of the Amyloid Protein Precursor (APP) in Alzheimer's Disease: Does the Normal Function of APP Explain the Topography of Neurodegeneration?," Neurochem. Res. 23(5):795-806 (1998).
Vickers JC, "A Vaccine Against Alzheimer's Disease: Developments to Date," Drugs Aging 19(7):487-494 (2002).
Cunningham et al., "Systemic Inflammation Induces Acute Behavioral and Cognitive Changes and Accelerates Neurodegenerative Disease," Biol. Psychiatry 65(4):304-12 (2009).
Cunningham et al., "Central and Systemic Endotoxin Challenges Exacerbate the Local Inflammatory Response and Increase Neuronal Death During Chronic Neurodegeneration," J. Neurosci. 25(40):9275-84 (2005).
Perry, "The Influence of Systemic Inflammation on Inflammation in the Brain: Implications for Chronic Neurodegenerative Disease," Brain Behav. Immun. 18(5):407-13.
Combrinck et al., "Peripheral Infection Evokes Exaggerated Sickness Behaviour in Pre-Clinical Murine Prion Disease," Neurosci. 112(1):7-11 (2002).
Sparwasser et al., "Bacterial CpG-DNA Activates Dendritic Cells In Vivo: T Helper Cell-Independent Cytotoxic T Cell Responses to Soluble Proteins," Eur. J. Immunol. 30:3591-7 (2000).
Zimmermann et al., "Cutting Edge: CpG Oligodeoxynucleotides Trigger Protective and Curative Th1 Responses in Lethal Murine Leishmaniasis," J. Immunol. 160:3627-30 (1998).
Rogers et al., "Metal and Inflammatory Targets for Alzheimer's Disease," Curr. Drug Targets 5(6):535-51 (2004).
Lahiri, "Molecular Analysis of the Promoter Region of the Gene Encoding the Beta-Amyloid Precursor Protein," Indian J. Biochem. Biophys. 32(6):329-35 (1995).
Yang et al., "Upregulation of Amyloid Precursor Protein Gene Promoter in Rat Primary Hippocampal Neurons by Phorbol Ester, IL-1 and Retinoic Acid, but not by Reactive Oxygen Species," Brain Res. Mol. Brain Res. 18(60):40-9 (1998).
Ge et al., "Regulation of Promoter Activity of the APP gene by Cytokines and Growth Factors: Implications in Alzheimer's Disease," Ann N Y Acad. Sci. 973:463-7 (2002).
Kitazawa et al., "Lipopolysaccharide-Induced Inflammation Exacerbates Tau Pathology by a Cyclin-Dependent Kinase 5-Mediated Pathway in a Transgenic Model of Alzheimer's Disease," J. Neurosci. 25(39):8843-53 (2005).
Schneider et al., "Hyperphosphorylation and Aggregation of Tau in Experimental Autoimmune Encephalomyelitis," J. Biol. Chem. 279(53):55833-9 (2004).
Ghosh et al., "Sustained Interleukin-1β Overexpression Exacerbates Tau Pathology Despite Reduced Amyloid Burden in an Alzheimer's Mouse Model," J. Neurosci. 33(11):5053-64 (2013).
Aguzzi et al., "Antiprion Immunotherapy: To Suppress or to Stimulate?," Nat. Rev. Immunol. 4:725-736 (2004).
Bremer et al., "Repetitive Immunization Enhances the Susceptibility of Mice to Peripherally Administered Prions," PLoS ONE 4(9):e7160 (2009).
Guillot-Sestier et al., "Innate Immunity in Alzheimer's Disease: A Complex Affair," CNS Nerol. Disord. Drug Targets 12(5):593-607 (2013).
Scholtzova et al., "Innate Immune Stimulation via Toll-Like Receptor 9 Ameliorates Vascular Amyloid Pathobiology in Tg-SwDI Mice with Associated Cognitive Benefits," J. Neurosci 37(4):936-959 (2017).
Selles et al., "Immunomodulation via Toll-Like Receptor 9: An Adjunct Therapy Strategy against Alzheimer's Disease?" J. Neurosci. 37(4):4864-4867 (2017).
Scholtzova et al., "Amyloid β and Tau Alzheimer's Disease Related Pathology is Reduced by Toll-like Receptor 9 Stimulation," Acta Neuropathol Commun. 2:101 (2014).
Alzoforum, "Inflammation Helps Microglia Clear Amyloid from AD Brains," (retrieved on Jul. 27, 2017 from http://www.alzoforum.org/news/conference-coverage/inflammation-helps-microglia-clear-a . . . ).
Restriction Requirement in U.S. Appl. No. 12/918,739 dated Aug. 9, 2012.
Office Action in U.S. Appl. No. 12/918,739 dated Oct. 10, 2012.
Office Action in U.S. Appl. No. 12/918,739 dated Apr. 23, 2013.
Office Action in U.S. Appl. No. 12/918,739 dated Nov. 21, 2013.
Office Action in U.S. Appl. No. 12/918,739 dated Jan. 27, 2015.
Office Action in U.S. Appl. No. 12/918,739 dated Aug. 13, 2015.
Office Action in U.S. Appl. No. 12/918,739 dated Sep. 2, 2016.
Office Action in U.S. Appl. No. 12/918,739 dated Mar. 20, 2017.
Communication for EP08785778.5 dated Jan. 11, 2018.
Intention to Grant for EP08785778.5 dated Aug. 16, 2018.
Restriction Requirement for U.S. Appl. No. 15/177,980 dated Mar. 9, 2017.
Office Action for U.S. Appl. No. 15/177,980 dated Jun. 16, 2017.
Office Action in U.S. Appl. No. 12/918,739 dated Dec. 28, 2017.
Office Action in U.S. Appl. No. 16/458,966 dated Jun. 26, 2020.

* cited by examiner

A

B

A

B

A

B

A

B

A

B

METHOD OF PROVIDING PATIENT SPECIFIC IMMUNE RESPONSE IN AMYLOIDOSES AND PROTEIN AGGREGATION DISORDERS

This application is a continuation of U.S. patent application Ser. No. 15/177,980, filed Jun. 9, 2016, which is a continuation of U.S. patent application Ser. No. 12/733,437, filed Jul. 22, 2010, now U.S. Pat. No. 9,370,531, issued Jun. 21, 2016, which is a national stage application under 35 U.S.C. § 371 of PCT Application Serial No. PCT/EP2008/007127, filed Sep. 1, 2008, which claims the benefit of European Patent Application Serial No. 07017135.0, filed Aug. 31, 2007, and U.S. Provisional Patent Application Ser. No. 60/967,178, filed Aug. 31, 2007, each of which are hereby incorporated by reference in their entirety.

The present invention relates to the treatment of diseases characterized by the appearance of neo-epitopes present in endogenous protein aggregates both being characteristic for a pathological status of a disease and to be selectively identified as disease antigen by the adaptive immune system. The present invention relates in particular to the treatment of Alzheimer's disease and disorders involving protein misfolding or aggregation by inducing an antibody response against at least one endogenous protein by the sole administration of at least one immunostimulant without need for co-administration of exogenous immunogen, whereby such antibody response is predominantly directed against neo-epitopes present on pathogenic forms of said protein or protein complex. Furthermore, the present invention concerns the use of immunostimulants to be administered ex vivo to antigen-selected peripheral blood lymphocytes that are subsequently re-grafted into the cognate donor. In addition, the present invention makes use of the therapeutic observations and includes methods of screening for novel binding molecules, which may or may not be antibodies, targets and drugs in the treatment of various disorders, in particular neurological disorders such as Alzheimer's disease and amyloidoses including beta-amyloid pathology.

BACKGROUND OF THE INVENTION

Alzheimer's disease ("AD") is the most common cause of age-related dementia and is a major cause of disability and death in the elderly. This disease, for which there is currently no effective cure, is a long-progressing, neurodegenerative disorder of the central nervous system characterized by increasingly debilitating, global cognitive defects including loss of memory, language deficits, and impaired judgment and abstract reasoning.

Post-mortem examination of brain tissue from AD patients reveals proteinaceous fibrils and filaments comprising extracellular plaques, vascular deposits of beta-amyloid, and intraneuronal neurofibrillary tangles. These fibrils and filaments comprise aggregates of a variant of the beta-amyloid precursor protein ("APP") called beta-amyloid-peptide (Abeta), and tau, respectively. Mutations or polymorphisms in the APP gene are found in patients with familial AD and are sufficient to increase in Abeta production in cultured cells, transgenic mice and human patients and, thus establishing a direct link between human gene variants and the disease pathology. Furthermore, more generally it is believed that abnormal depositions of amyloid proteins in brains result in amyloidosis which manifests itself in a variety of conditions, disorders, and diseases, Alzheimer's disease being one of the most prominent ones.

Presently there are no known effective treatments for preventing, delaying, halting, or reversing the progression of Alzheimer's disease and other conditions associated with amyloidosis. Consequently, there is an urgent need for methods of treatment capable of preventing and treating conditions associated with amyloidosis including Alzheimer's disease as well as other diseases.

Likewise, there is generally a need for methods of treatment of diseases and disorders that are caused by the accumulation of abnormal protein structures and peptide aggregation, in particular neurodegenerative diseases and also peripheral amyloidosis caused by abnormal protein aggregation, the so-called "protein aggregation disorders".

There is also a need for methods of treatment using compounds that are therapeutically effective in the mentioned disorders, substantially devoid of side effects, and which advantageously have already been proven in clinical tests for other medical indications.

As an example, current treatments of Alzheimer's disease with acetylcholine inhibitors rely on the replacement of acetylcholine, a memory-related neurotransmitter that decreases as a result of neurodegeneration. It is therefore a symptomatic treatment with no direct effect on the beta-amyloid deposition or the formation of neurofibrillary tangles. Acetylcholine esterase inhibitors can ameliorate the symptoms of dementia in some, but not all, patients for a limited amount of time. They are not considered a cure for Alzheimer's disease. Likewise, other currently used therapeutics including NMDA antagonists show some degree of efficacy in a subset of patients, but they do not affect the underlying pathology of Alzheimer's disease. Even though these symptomatic treatments can temporarily slow disease progression in some patients with Alzheimer's disease, causal treatments targeting the underlying beta-amyloid pathology are unavailable and urgently needed. Immunotherapy is among the most promising amyloid-lowering causal treatment approaches, but initial clinical vaccination trials were halted by subacute aseptic meningoencephalitis in 6% of the actively vaccinated patients (Orgogozo et al., Neurology 2003). Likewise, passive immunotherapy with monoclonal antibodies developed in mice can produce brain hemorrhages resulting in significant safety problems (Pfeifer et al., Science 2002). The development of safe and tolerable immunotherapy against beta-amyloid would thus be a major breakthrough in the future treatment of Alzheimer's disease. Initial signs for clinical efficacy of active vaccination were observed in follow-up studies of vaccinated patients (Hock et al., 2003). In analogy immunotherapy against pathological protein aggregates in other protein aggregation diseases including tauopathies, Parkinson's disease and Huntington's disease may be similarly safe and effective.

SUMMARY OF THE INVENTION

Object of the present invention is a method for inducing in a subject diagnostically and in particularly therapeutically useful binding molecules, in particular antibodies that are directed against pathologic variants and/or aggregation of endogenous proteins. The invention described here is based upon the unexpected observation that TLR agonists including, without limitation, CpG can intensify naturally occurring immune responses directed against endogenous pathological protein aggregates. In accordance with the present invention it is expected that stimulation of primed B lymphocytes with TLR agonists favors selective antibody responses against pathological protein aggregates over the normally occurring forms of precursor proteins. As a result, TLR agonists can intensify and sustain a naturally occurring but therapeutically ineffective immune response against pathological protein aggregates in a subject, which may be particular beneficial for the treatment of aged patients with compromised immune functions. In another embodiment, this approach will also be useful for disease prevention in healthy subjects with pre-clinical deposits of pathological protein aggregates.

The present invention relates to the use of an immunostimulant of the innate or adaptive immune system for the preparation of a pharmaceutical composition for the treatment, diagnosis, or prevention of disorders characterized by the deposition, in affected tissues, of pathological protein aggregates of endogenous or exogenous origin in human subjects or animals. Pathological aggregates typically contain neo-epitopes that are absent from the physiologically occurring form of the respective proteins, formed by misfolding, abnormal aggregation, often accompanied by dramatically reduced solubility due to pathologically altered three dimensional structure. In many cases, structural alternations are accompanied by increased half-life of the abnormal protein aggregate due to the inability of the physiological degradation machinery or proteases to degrade the aggregated material, accumulation in the affected tissue, association with many other proteins that adhere to the abnormal protein aggregate, loss of physiological functions of the cognate protein, or gain of toxic functions of the pathologic protein structure. Neo-epitopes shall mean epitopes that have escaped tolerance because of their abnormal structures, or recognizable by the immune system to be defined e.g. via specific reaction with a respective antibody that binds to the pathological protein aggregate, e.g. via recognition of its neo-epitopes.

More specifically, the present invention relates to the use of an immunostimulant of the innate or adaptive immune system for the preparation of a pharmaceutical composition for the treatment of a subject suffering from a disorder characterized by the presence of a pathological neo-epitope, in particular a pathological neo-epitope of at least one type of amyloidosis-creating fibrillar or plaque like form of protein/protein or protein/peptide or peptide/peptide aggregates.

The present invention is based on the novel and surprising finding that by enhancing or sustaining an antibody response against at least one endogenous protein by the sole administration of an immunostimulant without co-administration of exogenous immunogen Alzheimer's disease simulated in mouse model system can successfully enhance a selective antibody response for treatment, whereby such antibody response is predominantly directed against neo-epitopes present on pathogenic forms of said protein or protein complex. In this context, the immunostimulant may also be administered ex vivo to antigen-selected peripheral blood lymphocytes which can subsequently be re-grafted into the cognate donor and exert beneficial therapeutic effects.

The present invention relates to known classes of immunostimulants, particularly nucleic acids and derivatives thereof as well as low molecular weight agonists of the TOLL-like-receptor family (TLR), to enhance the innate or adaptive immune status of different effector functions and boost preexisting B-memory cells or B-cells to produce respective autoantibodies directed against pathological conformations of said proteins that are generated by way of example by misfolding, oligomerization, aggregation or complex formation of said proteins or, in a related application enhance the general immune systems effector functions if in a passive immunization such antibody or mixture of antibodies get co-administered, or in a related application enhance effector functions and efficiency of auto-vaccination against endogenous self-antigens with pathological conformations in aged subjects with compromised immune response, or in a related application, to stimulate TLR functions in peripheral blood lymphocytes ex vivo. Such amyloidoses primarily being associated with diseases such as neurodegenerative diseases, such as Alzheimer Disease, Down's syndrome, cerebral amyloid angiopathy, mixed dementia, or inclusion body myositis, glaucoma, or arteriosclerosis associated amyloidoses, or other forms of amyloidoses comprising fibrillaric proteins derived from at least one of the following precursor proteins SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Kerato-epithelin); ALac (Lactoferrin), Abri (AbriPP), ADan (ADanPP); or AANP (Atrial natriuretical peptide), or neurodegenerative diseases characterized by the deposition of abnormally aggregated forms of endogenous proteins including but not limited to beta-amyloid in Alzheimer's disease, Down's syndrome, cerebral amyloid angiopathy, hereditary cerebral hemorrhage with amyloidosis Dutch type and Icelandic type alpha-synuclein in Parkinson's disease, Alzheimer's disease, dementia with lewy body, multiple system atrophy; Prion protein in Creutzfeldt-Jakob disease and related prion diseases, Huntingtin in Huntington's disease, tau or other neurofibrillary tangle-related proteins in tauopathies including progressive supranuclear palsy (PSP), cortico-basal degeneration (CBD), agyrophilic grain disease (AGD), fronto-temporal dementia (FTD), frontotemporal dementia with Parkinsonism (FTDP17), Pick bodies in Pick's disease, ataxin in Spinocerebellar ataxia, copper/zinc super oxide dismutase in amyotrophic lateral sclerosis and TDP-43 in frontotemporal lobar degeneration and amyotrophic lateral sclerosis. In another embodiment, the stimulated immune response may also be directed against amyloid-associated proteins.

The therapeutic use of such immunostimulants in patients suffering from at least one of the above mentioned diseases to reverse, stabilize or prevent the development of such diseases is directed to boost the native immune response mediated to a large extent by B-cells and supported by T-cells whereby those B-cells will be activated which's surface bound immunoglobulins recognize neo-epitopes of disease-associated proteins detectable in abnormal conformation or deposits of amyloid or other abnormal protein aggregates composed of pathologic assemblies of monomeric constituents. Such monomeric constituents are derived or processed from native endogenous proteins and are prevalent in the body of a patient in a pathological variant form or associated in such pathological deposits as plaque like clusters and/or differently localized compared to their normal physiological subcellular localization and environment.

In addition, the present invention relates to pharmaceutical compositions comprising such immunostimulants alone or in combination with binding entities, antibodies and mimics thereof, and to methods of screening for novel binding entities, which may or may not be antibodies, targets and drugs in the treatment of various disorders, in particular neurological disorders such as Alzheimer's disease and beta-amyloid pathology and amyloidoses and protein aggregation diseases in general.

The present invention is also based upon the observation that aging is associated with decreased immune surveillance functions, while aging is the most important risk factor for the deposition of pathologic protein aggregates including beta-amyloid. Thus, the age-related increased in risk for amyloidosis could be paralleled by an age-related decrease in the immune system's capacity to detect, and remove such deposits. Stimulating the immune system with methods described herein is expected to reduce such age-related developments.

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. The term "pathological neo-epitope" refers to an epitope characteristic for the status of a disease or pathological phenotype; see also supra.

For the sake of clarity, and in case of ambiguity the following definitions of terms apply:

Abeta=amyloid beta-peptide=the monomeric peptides (Abeta1-40 and Abeta 1-42 and additional minor forms).

Abeta oligomers=all soluble and insoluble oligomeric assemblies of monomeric Abeta peptides.

Abeta fibrils=beta-amyloid fibrils=all fibrillar assemblies of Abeta peptides, mostly insoluble.

beta-amyloid=large accumulations of Abeta fibrils and Abeta oligomers in senile plaques and congophilic amyloid angiopathy.

APP=beta-amyloid precursor protein, precursor of all Abeta peptides.

Senile plaques=contain insoluble beta-amyloid fibrils and Abeta oligomers, Congo-red- and ThioS-positive, and TAPIR-positive, i.e. as determined by the method of monitoring immunotherapy coined tissue amyloid plaque immunoreactivity (TAPIR) assay as described in international application WO2004/095031; see also infra.

Diffuse plaques=contain soluble Abeta and soluble Abeta oligomers, no fibrils, Congo-red and Thio S negative, only TAPIR-positive.

CAA=congophilic amyloid angiopathy=beta-amyloid fibrils around blood vessels Congo-red- and ThioS-positive, and TAPIR-positive.

DETAILED DESCRIPTION OF THE PRESENT INVENTION

Figure 1:
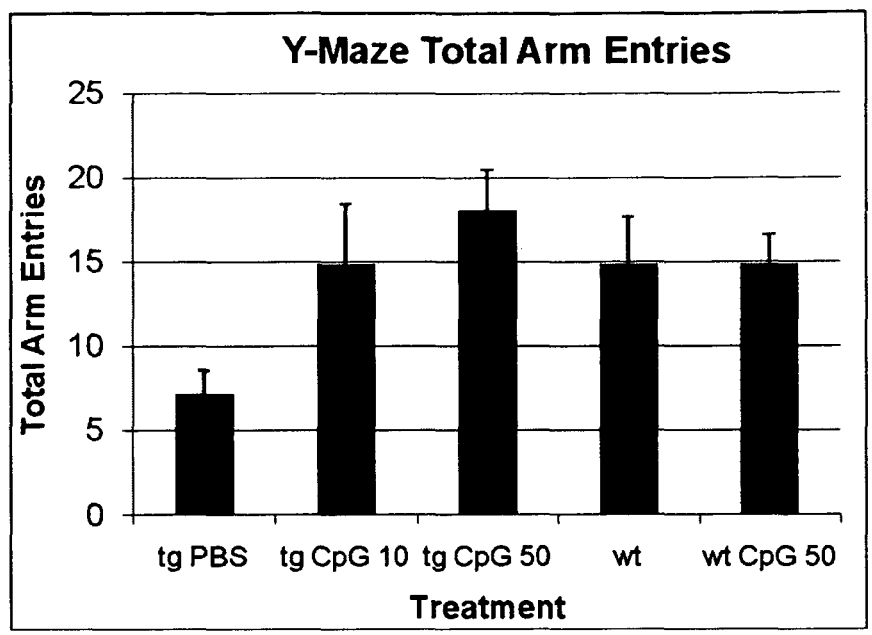
FIG. 1: Behavior of CpG-treated mice in the Y-maze. A. Number of total arm entries. B. Alternations as percentage of total arm entries. Treatment with either 10 or 50 µg of CpG resulted in an increased number of arm entries as well as percent alternation in APPsweArc transgenic mice indicating improved exploratory activity and working memory upon treatment with CpG
Figure 1:
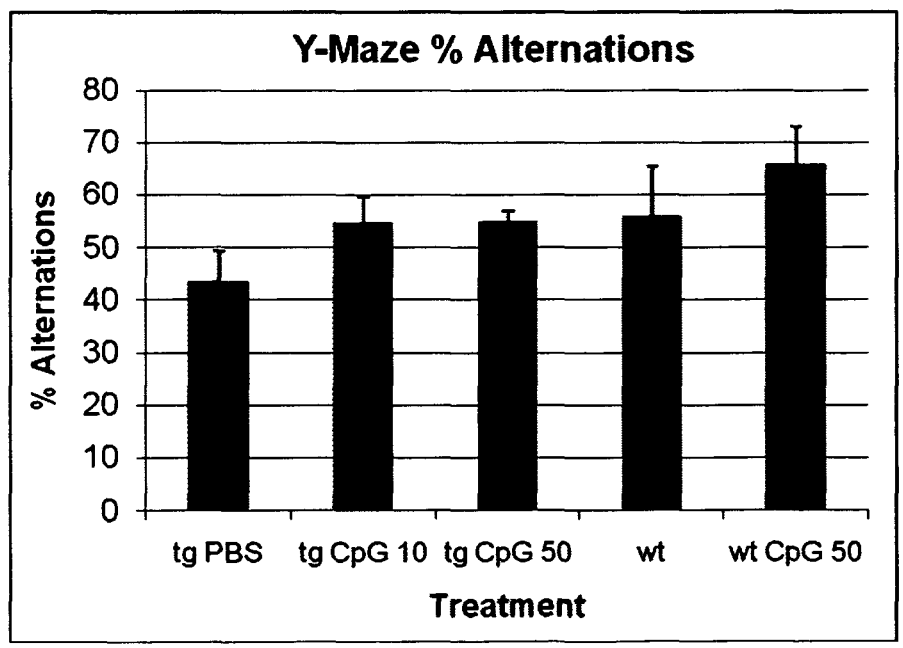

In one aspect the present invention relates to a method for enhancing a natural occurring immune response directed against pathological conformations of endogenous proteins that are generated by way of example by protein misfolding, oligomerization, aggregation, complex formation or the formation of plaque, fibrillar or inclusion body structures as is observed in various types of amyloidoses and neurodegenerative diseases. In particular, the present invention relates to the use of an immunostimulant of the innate or adaptive immune system for the preparation of a pharmaceutical composition for the treatment of a subject suffering from a disorder characterized by the presence of a pathological neo-epitope of at least one type of amyloidosis-creating fibrillar or plaque like form of protein/protein or protein/peptide or peptide/peptide aggregates.

Put in other words, but without intending to be bound by theory, the therapeutic approach present invention may be characterized to induce autoantibodies which specifically recognize amyloidosis associated fibrillar or plaque like forms of protein/protein, protein/peptide or peptide/peptide aggregates and structures, respectively.

In this respect, one surprising finding in accordance with the present invention is that the compounds to be used for novel therapeutic approach are capable of inducing a rather specific antibody response while not leading to an overactive immune system which could harm the body and result in an autoimmune disease such as Lupus erythematosus. Moreover, since many of the compounds such as CpG and the like intended for the pharmaceutical compositions of the present invention have already been tested in clinical trials and turned to be safe, there is even proof that side effects may not be expected and thus the therapeutic approach of the present invention can be clinically tested as soon as possible. In this context it is to be understood that the treatment regimen and dosage for the therapeutic approach of the present invention may substantially follow those described for CpG and the like compounds in the treatment of protein aggregation diseases and amyloidoses including, without limitation, Alzheimer's disease, Down's syndrome, cerebral amyloid angiopathy, hereditary cerebral hemorrhage with amyloidosis Dutch type and Icelandic type, mixed dementia, dementia with lewy body, multiple system atrophy; inclusion body myositis, glaucoma, Amyotrophic lateral sclerosis, Spinocerebellar ataxia, Parkinson's disease, Huntington's disease, dementia with Lewy bodies, Tauopathies including progressive supranuclear palsy (PSP), cortico-basal degeneration (CBD), agyrophilic grain disease (AGD), fronto-temporal dementia (FTD, frontotemporal dementia with Parkinsonism (FTDP17), frontotemporal lobar degeneration, Creutzfeldt-Jakob and related prion diseases, Morbus Pick, familial amyloid polyneuropathy and amyloidoses comprising fibrillaric proteins derived from at least one of the following precursor proteins: Tau, alpha-synuclein, huntingtin, ataxin, superoxide dismutase, TDP-43, SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Kerato-epithelin); ALac (Lactoferrin), Abri (AbriPP), ADan (ADanPP); or AANP (Atrial natriuretical peptide); for review see, e.g., Skovronsky at al., Annu. Rev. Pathol. Mech. Dis. 1 (2006), 151-70 and Buxbaum, Curr. Opin. Rheumatol. 16 (2003), 67-75.

It has been shown by various authors that antibodies or the existence of antibodies against beta-amyloid-related proteins can be detected in elderly subjects as well as in patients with Alzheimer's disease which might be related to a slower progression of Alzheimer's Disease in such patients (see also Brettschneider et al., Biol. Psychiatry 57 (2005), 813; Moir et al., J Biol Chem 280 (2005), 17458-17463; Song et al., J. Int. Med. Res. 35 (2007), 301-306). Inasmuch as such endogenously occurring antibodies have the ability to penetrate into the brain over the blood brain barrier, and inasmuch as such antibodies are active in removing abnormal and pathologic protein aggregates, including but not limited to beta-amyloid from brain, such antibodies might be related to endogenous prevention or to slower progression rates of Alzheimer's disease in such subjects. It could also be demonstrated that antibodies cloned from human patients as well as antibodies generated in vitro or in mouse model systems, as well as human beta-amyloid antibodies present in commercial IVIg preparations (Weksler et al., Cornell University) are able to lower the amyloid plaque load in mouse model systems generating human-like beta-amyloid plaque structures from human disease-causing mutants of the beta-amyloid precursor protein. Various strategies are currently under clinical and preclinical investigation to determine the pharmacological usefulness of such kind of antibodies given as passive immunization in the treatment of Alzheimer's disease. Strategies of active immunization have failed so far as the immune system generates a number of antibodies and T-cell responses against different epitopes, some of them of potentially beneficial value, others with potentially detrimental effects by even enhancing the amyloid plaque load or the re-deposition of amyloid from neuropil as plaques to blood vessels, or by inducing subacute aseptic meningoencephalitis and related forms of autoimmunity. Another inherent risk associated with active immunization is the generation of antibodies directed against endogenous self-epitopes present on physiologically occurring epitopes present in linear or structural epitopes of monomeric Abeta peptides or aggregated structures thus leading to antibodies cross-reacting with natively processed forms of physiological amyloid precursor protein (APP) derivatives including Abeta, and potentially leading to an autoimmune disease of yet unknown nature.

Hence, the therapeutic approach of the present invention is particular advantageous in the treatment of elderly subjects since many patients of advanced age suffer from a disease because of an insufficient immune response to the disease causing agent. In accordance with the present invention, an appropriate immune response against a pathological protein/peptide and protein/peptide structure can be induced and/or boosted so as to bringing the patient to a state of being capable of combating those pathological neo-epitope containing agents like younger people can do.

The status of the immune system in elderly patients is known to functionally decline both in its capability to generate, optimize and produce relevant antibodies and to support the antibody-mediated functions such as effector functions which very much depend on the integrity of the innate or adaptive immune response. It would be desirable to selectively raise an autoimmune response against such neo-epitopes but avoiding a major autoimmune response against physiological, functionally relevant, epitopes such as, for example, physiologically generated derivatives of APP, including Abeta. It would also be beneficial to enhance a basic but inefficient preexisting immune response via immunoglobulins selectively directed against neo-epitopes of such mentioned structures present in abnormal, pathologic, protein aggregates including but not limited to amyloid-fibrillary structures, inclusion bodies in both elderly and young patients, as well as, in a preventive application, in healthy subjects who are at risk of developing a protein aggregation disorder later in life. It would be also beneficial, too, if such antibody or a combination of antibodies applied as a drug could be functionally enhanced, and it would be beneficial, if antigen-specific B cells would be activated to differentiate into IgG-producing plasma cells.

Hence, one further advantage of the therapeutic approach of the present invention is that concomitant administration or vaccination is not required because the induction of the endogenously primed immune system is targeted. Therefore, in one embodiment of the present invention the pharmaceutical composition employed does not comprise an antigen having said pathological neo-epitope. Likewise, in addition or alternatively, the pharmaceutical composition in the use of the present invention is designed to be administered to a subject who has not been vaccinated with an antigen having said pathological neo-epitope. Such co-administration might even be prone to risk as Lee et al. (Ann. Neurol. 58 (2005), 430-435) have observed that antibodies might preferentially be triggered to non-conformational epitopes, potentially present on physiologically processed proteins or peptides.

Disorders amenable to the therapeutic approach of the present invention can preferably be diagnosed by applying the TAPIR assay, i.e. the method of monitoring immunotherapy as described in international application WO2004/095031 on various specimens of amyloidic tissue out of the group of amyloidoses such as Alzheimer Disease, Morbus Pick, Down's syndrome, cerebral amyloid angiopathy, mixed dementia, inclusion body myositis, glaucoma or Arteriosclerosis associated Amyloidoses, or neurodegenerative diseases characterized by the deposition of abnormally aggregated forms of endogenous proteins including but not limited to beta-amyloid in Alzheimer's disease, Down's syndrome, cerebral amyloid angiopathy, hereditary cerebral hemorrhage with amyloidosis Dutch type and Icelandic type, alpha-synuclein in Parkinson's disease, Alzheimer's disease, dementia with lewy body, multiple system atrophy; Prion protein in Creutzfeldt-Jakob disease and related prion diseases, Huntingtin in Huntington's disease, tau or neurofibrillar-tangle associated proteins in Tauopathies including progressive supranuclear palsy (PSP), cortico-basal degeneration (CBD), agyrophilic grain disease (AGD), fronto-temporal dementia (FTD, fronto-temporal dementia with Parkinsonism (FTDP17), Alzheimer's disease Picks disease; ataxin in Spinocerebellar ataxia and copper/zinc super oxide dismutase in Amyotrophic lateral sclerosis and TDP-43 in frontotemporal lobar degeneration and amyotrophic lateral sclerosis. In another embodiment, the stimulated immune response may also be directed against amyloid-associated proteins or other forms of Amyloidoses comprising fibrillaric proteins derived from at least one of the following precursor proteins SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Kerato-epithelin); ALac (Lactoferrin), Abri (AbriPP), ADan (ADanPP); or AANP (Atrial natriuretical peptide) have demonstrated to be associated with the presence of antibodies against respective protein aggregates structures in a variety of patients.

In some disorders to be treated in accordance with the present invention said neo-epitope comprises or consists of a conformational epitope formed after upon oligomerization or fiber formation or an epitope formed by one of the fibril forming peptides associated with at least one different peptide or molecular entity in a heteromeric complex. Disorders commonly associated and/or caused by such oligomerization include but are not limited to Alzheimer Disease, amyloid deposition associated with aging, mild cognitive impairment, Down's syndrome, cerebral amyloid angiopathy, mixed dementia, inclusion body myositis, glaucoma, Morbus Pick, arteriosclerosis, Parkinson's disease, multiple system atrophy, corticobasal degeneration, frontotemporal lobar degeneration, Huntington's disease, tauopathy, and Pick's disease, head trauma, dementia pugilistica, chronic traumatic encephalopathy, cerebral amyloid angiopathy, Creutzfeldt-Jakob disease, cystic fibrosis, or Gaucher's disease.

As could be demonstrated in the appended examples administering the immunostimulant CpG to mice displaying severe symptoms of Alzheimer's disease and in particular amyloidosis resulted in amelioration of Aβ plaque load and improved behavior of the animals. Thus, CpG therapy seems to be of particular advantage for the treatment of patients suffering from an advanced progression of the disorder. Accordingly, in one embodiment of the present invention the immunostimulant is designed to be administered after the onset of the disorder at a clinical stage, preferably to a subject characterized by amyloid plaque load in the brain and showing classical symptoms of Alzheimer's disease such as impaired memory.

On the other hand, without intending to be bound by theory it is believed that an immune response in a subject present at an early stage of the development of the disorder may help to overcome the disorder, slow its progression and/or prevent the development of severe symptoms of the disease. Hence, in the experiments performed in accordance with the present invention it could be shown that the level of autoantibodies strongly increases after CpG treatment. Thus, early therapeutic intervention with CpG also holds great promise as a preventive treatment of for example Alzheimer's disease. Accordingly, in another embodiment of the present invention the immunostimulant is designed to be administered at a subclinical stage of the disorder, e.g. amyloidosis, in particular brain amyloidosis in non-demented individuals.

In accordance with the present invention and deduced from the experimental considerations below the immunostimulant to be used for inducing the innate or adaptive immune system of a subject is a TOLL-like-receptor agonist. Without intending to be bound by theory it is believed that stimulants of the innate or adaptive immune system such as CpGs or stabilized immune modulatory RNA (SIMRA) compounds agonistically interacting with at least one of the three TOLL-like receptors TLR7, TLR8 or TLR9, as described in Davis et al. in U.S. Pat. No. 6,406,705 and in Tao et al., PNAS USA 104 (2007), 13750-13755, might have the potential of stimulating residual respective B-cells in order to stimulate the generation of respective antibodies to address such pathological protein epitopes or plaque structures with the consequence of lowering the concentration of such pathologically altered proteins or protein aggregates or plaques in a patient as a causal therapy or to activate antigen-selected B-cells ex vivo, that subsequently differentiate into IgG-secreting plasma cells upon re-grafting into the cognate donor. Unmethylated CpG motifs as well as SIMRA seem to be native potent activators of the innate or adaptive immune system associated with the recognition of, and defense against, general microbial or viral infections. The invention refers to auto-vaccination against neo-epitopes, however, without administering a compound which contains such said neo-epitope, however, in a preferred application to be combined with a mAb directed against such neo-epitope, and, in a related application the ex-vivo use of said immunostimulants in antigen-selected lymphocytes.

CpG motifs able to agonistically interact with TOLL-like receptors TLR 9 receptor are known to enhance the activation status of the innate or adaptive immune system (Lanzavecchia and Sallusto, Curr. Opin. Immunol. 19 (2007), 268-274), and SIMRA compounds stimulate TLR-7,-8 and TLR 8 (Tao et al., 2007, supra). Any such activity, however, is absolutely contraindicative in cases of autoimmune diseases such as Lupus erythematosus, which might be successfully addressed by administration of inhibitors of such TOLL-like receptors TLR-7, -8 or TLR-9. With antibodies reactive against endogenously occurring beta-amyloid-plaques or oligomeric or aggregated Abeta peptides identified in patients with Alzheimer's disease, it may seem that such patients have the status of a protective autoimmune reaction. Naturally occurring antibodies directed against a naturally occurring protein structure could have undesired effects as such APP-derived proteins and peptides are expressed in different tissues and have widely unknown functionality. Any stimulation of TLR-7 or TLR-9 could have negative consequences if such respective B-memory cells would be positively triggered to proliferate and to produce antibodies. In particular, antibodies generated against Abeta-peptides by applying such peptides as vaccines seem to predominantly react with linear epitopes of such peptides (Lee et al., 2005 Ann. Neurol. 58 (2005), 430-435). If such naturally occurring antibodies or antibody producing B-cells, respectively, would be enhanced in their activity, a non-desired autoimmune response against natively processed APP derivatives including Abeta is expected to be induced. This autoimmune phenomenon not being a major issue in human patients anyway might relate to the status in elderly patients with an immune system of just 10 to 20% of its normal activity in young patients. Because the structural neo-epitopes generated during pathologic aggregation of the physiologically occurring APP derivatives or Abeta peptides, however, such response may also be seen as an immune response directed against an endogenously generated pathological structure, resulting in a preventive—or therapeutic—neutralization or removal of such pathological structures. Naturally occurring antibodies are directed against a naturally occurring, but pathological protein structure.

In view of the above considerations, in one preferred embodiment the present invention relates to the use of an immunostimulant comprising at least one oligonucleotide or modified oligonucleotide containing at least one unmethylated CpG dinucleotide motif for the treatment of a subject suffering from a disorder characterized by the presence of a pathological neo-epitope or protein aggregate as defined above.

Furthermore, in some embodiments, the pharmaceutical composition prepared in accordance with the present invention comprises or is designed to be applied in combination with at least one binding molecule directed against at least said one neo-epitope, preferably wherein said binding molecule is an antibody, typically of the IgG type, preferentially a human IgG.

Such endogenous proteins providing neo-epitopes/aggregates belonging to Alzheimer Disease, amyloid deposition associated with aging, mild cognitive impairment, head trauma, dementia pugilistica, chronic traumatic encephalopathy, Morbus Pick, Down's syndrome, cerebral amyloid angiopathy, mixed dementia, inclusion body myositis, glaucoma or Arteriosklerosis associated Amyloidoses, or neurodegenerative diseases characterized by the deposition of abnormally aggregated forms of endogenous proteins including but not limited to beta-amyloid in Alzheimer's disease, amyloid deposition associated with aging, mild cognitive impairment, Down's syndrome, cerebral amyloid angiopathy, hereditary cerebral hemorrhage with amyloidosis Dutch type and Icelandic type, alpha-synuclein in Parkinson's disease, Alzheimer's disease, dementia with lewy body, multiple system atrophy; Prion protein in Creutzfeldt-Jakob disease and related prion diseases, Huntingtin in Huntington's disease, tau or neurofibrillar-tangle associated proteins in Tauopathies including progressive supranuclear palsy (PSP), cortico-basal degeneration (CBD), agyrophilic grain disease (AGD), fronto-temporal dementia (FTD, fronto-temporal dementia with Parkinsonism (FTDP17), Picks disease; ataxin in Spinocerebellar ataxia copper/zinc super oxide dismutase in Amyotrophic lateral sclerosis and TDP-43 in frontotemporal lobar degeneration and amyotrophic lateral sclerosis. In another embodiment, the stimulated immune response may also be directed against amyloid-associated proteins, or other forms of amyloidoses comprising at least one of the following precursor proteins SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Keratoepithelin); ALac (Lactoferrin), Abri (AbriPP), ADan (ADanPP); or AANP (Atrial natriuretical peptide). Such human antibodies can be applied to treat patients suffering from amyloidoses in order to either complement a non-functioning human immune response or to strengthen and complementary support a non-sufficient immune response alone or in combination with different antibodies.

In a further embodiment of the present invention, such antibodies can also be applied in combination with immunostimulants such as CpG as agonist of at least TOLL-like 9 receptor and derivatives as described by, e.g., Krieg et al. in US patent application publication no 2007/0066554 and Davis et al. in U.S. Pat. No. 6,406,705. Instead of CpG type immunostimulants other immunostimulants can be applied as well as long as they agonistically interfere with the binding to at least TOLL-like 9 receptor.

As at least one type of immunostimulant of the innate or adaptive immune system in elderly patients in clinical trials against Non Small Cell Lung Carcinoma (NSCLC) suffering from at least one form of amyloidosis oligonucleotides have been applied comprising at least one non-methylated CpG-motif, such as Coley Pharmaceutical's ProMune™ which is CPG 7909, a B-Class CpG ODN. Hence, a large class of CpG compounds is available from/described in patent applications by Coley Pharmaceuticals, thus a collection from which alternative oligonucleotides can be applied with similar results in order to enhance the adaptive immune response against neo-epitopes of at least one type of amyloidosis-creating fibrillar form of protein plaques or to support the function of antibodies directed against such neo-epitopes. The quantity and quality of antibody response enhanced by administering at least one type of said oligonucleotide comprising at least one non-methylated CpG motif was measured by means of the TAPIR-assay. As described, the TAPIR assay makes use of the presence of pathogenic forms of such protein clusters providing such neo-eptitopes for antibody binding.

By staining such bound human antibody, such as IgG, by e.g. fluorescently labeled anti-human IgG such antibodies can be visualized and semi-quantitatively differentiated from stainings of samples derived from mice not treated with CpG-motif type oligonucleotides in respective formulations. According to the present invention alternative immunostimulants alone or in combination can be applied whereas at least one of such active compounds belongs to the group of TOLL-like receptor agonists of at least one of the receptor subtypes such as TOLL-like receptor-9 (TLR-9).

In a preferred embodiment of the present invention, the pharmaceutical composition to be used comprises at least one non-nucleic acid adjuvant capable of creating a depo effect. Typically, at least one type of immunostimulant of the innate or adaptive immune system is applied together with an adjuvant of at least one ingredient as described by Krieg et al. in US patent application publication no 2007/0066554 and Davis et al. in U.S. Pat. No. 6,406,705, whereby the at least one immunostimulant comprises at least one non-nucleic acid adjuvant that creates a depo effect. In one embodiment the adjuvant is selected from the group consisting of alum, emulsion based formulations, mineral oil, non-mineral oil, water-in-oil emulsions, water-in-oil-in-water emulsions, Seppic ISA series of Montanide adjuvants, MF-59, and PROVAX. Preferably, the adjuvant comprises an immune stimulating adjuvant. A particular effective combination in the inventive procedure is the combination of CpG motifs with Vitamin A to drive memory B cells into Ig-secreting plasma cells (see Ertesvag et al. Blood 109 (2007), 3865-3878) at serum concentrations between 1 nM to 100 nM.

Preferably, administration of CpG-type reagents are co-administered with an adjuvant that creates a depo effect such adjuvant being selected from the group consisting of alum, emulsion based formulations, mineral oil, non-mineral oil, water-in-oil emulsions, water-in-oil-in-water emulsions, Seppic ISA series of Montanide adjuvants; MF-59; or PROVAX. As an adjuvant we typically administer a non-nucleic acid adjuvant which is selected from the group consisting of saponins, PCPP polymer; derivatives of lipopolysaccharides, MPL, MDP, t-MDP, OM-174 and *Leishmania* elongation factor.

In addition, or alternatively, agents are preferably used which create both, a depo effect and an unspecific stimulation of the immune system at the same time. Such group of compounds consists of ISCOMS or SB-AS2 or AS2 or SB-AS4 or non-ionic block copolymers and SAF. The composition of the therapeutically applied mix of components might also include an antigen that is selected from the group of amyloid forming peptides. In a particular application such antigens are offered as preformed aggregates providing said conformational binding sites as neo-epitopes. Such reagents seem to help booster preexisting memory B cells or respective plasma cells to be either stimulated for replication or for further maturation or class switches of respective antibodies recognizing such neo-epitopes. Hence, in some embodiments of the present invention it may be preferred include into the pharmaceutical composition an antigen having a neo-epitope as defined for any disease hereinabove.

In a further aspect of the present invention, such immunostimulant treated patients can be seen as a potent source of antibodies and their coding cDNAs directed against such neo-epitopes, mediated by B-cell cloning as described in Bernasconi et al. (2002) or in particular in international application WO2008/081008, the disclosure content of which is incorporated herein by reference, including the identification and cloning of respective IgG coding sequences, their isolation, and use to construct expression vectors for the production of respective antibodies, in particular of IgG of various subtypes-1, 2, -3, or -4, validating and producing diagnostically and therapeutically useful binding molecules, in particular antibodies that are directed against pathologic variants of endogenous proteins with their neo-epitopes.

As mentioned and described in the examples in accordance with the present it turned out that antibodies effective to counteract progressive amyloidoses typically react with neo-epitopes of plaque structures instead of reacting with precursor forms of monomeric proteins as physiologically processed entities. The TAPIR assay described in international application WO2004/095031 allows selectively differentiating between both such types of antibodies according to selective staining of such polymeric pathological structures as specific structural entities not detectable in sections of specimen from healthy regions. Such neo-epitopes seem to preferentially represent conformational epitopes which just form upon polymerization of fiber structures alone or in close association with other molecular entities.

In particular, as a novel observation, mice with heavily loaded plaques of beta-amyloid-fibers in respective brain regions as described in Knobloch et al., Neurobiol. Aging July 28 (2006) show substantial decreases of plaque load comparing CpG-treated mice and non-CpG-treated mice obviously mediated or associated with the appearance of neo-epitope recognizing antibodies or their enhanced effective concentration at the site of action. Without intending to be bound by theory it is believed that in accordance with the present invention CpG assists in or mediates the activation of B-cells or B-memory cells, in respect to amyloidoses B-cells primarily reacting to neo-epitopes of such polymeric structures and to not significantly cause an autoimmune response against non-neo-epitopes. However, the Co-administration of TOLL-like-receptor agonists with an active immunization approach might be contraindicative for the therapeutic treatment of human patients as it is known that such vaccination might lead to antibodies recognizing linear epitopes as also being part of natively processed proteins (Lee et al., 2005, supra). The surprising finding of the novel therapeutic approach of the present invention is the successful treatment of e.g. Alzheimer's disease with the characteristic of also belonging to the group of protective autoimmune diseases as creating an antibody response against at least one of a patient's own protein by at least one immunostimulant whereby such patient own antibodies are predominantly directed against neo-epitopes expressed on pathogenic forms of said protein or protein complex.

A clonal or oligo-clonal in vivo expansion of such therapeutically relevant type of B-cell or B-cells recognizing at least one neo-epitope does not only contribute positively in terms of a therapeutic effect in said patients treated but also provides or facilitates the experimental basis to in vitro select such B-cells from patient's blood samples, temporarily stabilize or immortalize such B-cells, characterize their respective antibodies identified, preferably by the TAPIR assay, see supra, and generate a cDNA clone coding for such antibody, all such steps performed as described in detail in international application WO2008/081008, supra.

Hence, in a further aspect the present invention relates to a method of producing a neo-epitope specific binding molecule as defined above from a sample of a mammal, wherein prior to obtaining the sample a pharmaceutical composition as hereinbefore has been administered to the mammal. Said method preferably comprises determining the binding of a binding molecule to a specimen neo-epitope by an assay based on the detection of pathogenic forms of plaques or fibrillar aggregates via recognition of said pathological neo-epitope such as via the TAPIR assay or assays derived thereof, and optionally isolating the binding molecule so identified. In addition, the mammal used as the source for the sample to be analyzed preferably has overcome a disorder or the progression of said disorder. This is because in accordance with the findings of the present invention it is prudent to expect that such a mammal possesses B cells and memory B cells which are capable of secreting antibodies which protect the mammal against onset, progression or relapse of the disorder mediated by the accumulation of oligomerized proteins and peptides, respectively.

In a particular preferred embodiment of the present invention said mammal has suffered from a neurodegenerative disease in particular Alzheimer's disease. In addition, or alternatively, said mammal may or may not have been treated in accordance with therapeutic use and method of the present invention. In a particular preferred embodiment the mammal is a human.

Typically, said sample comprises a body fluid or a cell sample, e.g. urine, blood, lymph or cerebrospinal fluid or subfractions thereof. As evident from the examples the binding molecule is preferably an antibody and thus the sample will usually comprise or consist of B-cells or memory B-cells, or cells derived thereof.

In a further embodiment, the method of the present invention further comprises the steps of:
  (i) purifying B cells or B memory cells from a sample which has been identified to contain binding molecules, i.e. antibodies which bind to a neo-epitope specimen but not or substantially less to a corresponding control specimen without said neo-epitope;
  (ii) obtaining the immunoglobulin gene repertoire for said antibodies from said B cells or B memory cells; and
  (iii) using said repertoire to express said antibodies, and optionally wherein step (ii) comprises the steps of:
  (iv) obtaining mRNA from said B cells or memory B cells;

(v) obtaining cDNA from the mRNA of step (iv); and
(vi) using a primer extension reaction to amplify from said cDNA the fragments corresponding to the heavy chains (HC) and the kappa/lambda light chains (LC) of said antibodies.

As mentioned, methods of producing clones of an immortalized human B cell and B memory lymphocyte, comprising the step of transforming human B memory lymphocytes using Epstein Barr Virus (EBV) in the presence of a polyclonal B cell activator are summarized in international application WO2004/076677. This international application also describes methods for obtaining a nucleic acid sequence that encodes an antibody of interest, comprising the steps of preparing an immortalized B cell clone and obtaining/sequencing nucleic acid from the B cell clone that encodes the antibody of interest and further inserting the nucleic acid into or using the nucleic acid to prepare an expression host that can express the antibody of interest, culturing or subculturing the expression host under conditions where the antibody of interest is expressed and, optionally, purifying the antibody of interest. It goes without saying that the nucleic acid may be manipulated in between to introduce restriction sites, to change codon usage, and/or to add or optimize transcription and/or translation regulatory sequences. All this techniques are state of the art and can be performed by the person skilled in the art without undue burden.

In this context, the present invention also relates to a binding molecule obtainable by the method of the present invention described herein, preferably which is capable of selectively recognizing a neo-epitope of a disorder-associated protein or peptide. Advantageously, the binding molecule of the present invention does not substantially recognize said protein in its non-disorder-associated form. Typically, the binding molecule is an antibody or an antigen binding fragment thereof, most preferably it is a human antibody.

Like in other immunoassays and therapeutic uses the binding molecule can be detectably labeled, for example with a detectable label selected from the group consisting of an enzyme, a radioisotope, a fluorophore and a heavy metal. Alternatively, or in addition the binding molecule may be attached to a drug.

Furthermore, the present invention relates to a composition comprising the binding molecule identified and obtained in accordance with the method of the present invention. In one embodiment, the composition is a pharmaceutical composition and further comprises a pharmaceutically acceptable carrier. Preferably, the pharmaceutical composition is designed for the treatment of Alzheimer's disease or amyloidosis, and optionally further comprises an additional agent useful for treating Alzheimer's disease, selected from the group consisting of small organic molecules, anti-Beta-amyloid antibodies, and combinations thereof.

According to this invention, such cloned antibodies directed against at least one type of neo-epitope preferentially characteristic for said amyloid plaque in at least one said type of Amyloidosis or protein aggregation disorder, respective antibody fragments or other kind of or modified form of antibody fragment containing entities derived from such cloned antibody alone or in combination with other biologically active compounds can be co-administered with CpG-type compounds as agonists of at least TLR 9 receptor in order to successfully treat patients suffering from such respective disease. Such antibodies can directly support via effector functions respective T-cell activities or activities of monocytic type of cells (e.g. dendritic cells or microglia cells), primarily via induction Fc receptor mediated phagocytosis or ADCC or CDC effector functions which seem to be needed to prevent or reverse the formation of such amyloidic plaques. An alternative to apply a TLR-9 agonist, other TLR-agonists might be applied as well such as TLR-4 agonists or TLR-7 or TLR-8 agonists as described in Davis et al. and Tao et al. cited hereinbefore.

In another embodiment of the present invention, the stimulated immune response will be initiated by stimulating antigen-selected peripheral blood lymphocytes ex vivo, and subsequently re-graft the autologous activated B-cells into the cognate donor. Thus, the present invention further relates to the use of use of B-cells and memory B-cells, respectively, as defined in and obtainable as an intermediate product from a patient in the method of the present invention hereinbefore for use as an autologous transplant in the preparation of a pharmaceutical composition for the treatment of a disorder as defined herein, wherein said B-cells being enriched by e.g. Leukapheresis and/or sorted for binding to a neo-epitope of amyloid plaques or its secreted product for binding to a neo-epitope as part of a plaque or fibrillar structure of proteins or peptides, potentially expanded and designed to be subsequently re-administered to said patient together or without further application of an immunostimulant.

Hence, the present invention generally relates to methods of treating neurological disorders characterized by abnormal accumulation and/or deposition of a protein/peptide in the central nervous system, which method comprises administering to a subject in need thereof a therapeutically effective amount of the pharmaceutical composition or ex vivo stimulated B cells as herein.

In this context, the general use of immunostimulants is envisaged, in particular CpG-motifs, such as CpG 1826 as active substance (see also Davis et al., J. Immunol. 160 (1998), 870-876; Hartmann et al., J. Immunol. 164 (2000), 944-953; Hartmann et al., J. Immunol. 164 (2000), 1617-1624; and Davis et al., supra) in order to treat patients of multiple types of amyloidoses as listed above by stimulating a not yet detectable or already detectable immune response selectively against neo-epitopes of otherwise natively processed monomers of the patient affected by such type of disease.

As mentioned, in an alternative embodiment such in vivo animal model systems or human patients suffering from amyloidoses might be treated with CpG in order to activate B-cell and B-memory cells, to be cloned and tested for selectively interacting with beta-amyloid-plaque structures and those reacting positively to be re-transplanted as autotransplant back to the patient.

However, the present invention is not limited to amyloidoses or amyloidoses created by polymers derived from processed beta-amyloid-monomeric peptides but also to amyloidoses associated with Morbus Pick, Down's syndrome, amyloid deposition associated with aging, mild cognitive impairment, head trauma, dementia pugilistica, chronic traumatic encephalopathy, cystic fibrosis, Gaucher's disease, cerebral amyloid angiopathy, mixed dementia, inclusion body myositis, glaucoma or arteriosclerosis associated amyloidoses, or neurodegenerative diseases characterized by the deposition of abnormally aggregated forms of endogenous proteins including but not limited to alpha-synuclein in Parkinson's disease, Alzheimer's disease, dementia with lewy body, multiple system atrophy; Prion protein in Creutzfeldt-Jakob disease and related prion diseases, huntingtin in Huntington's disease, tau or neurofibrillar-tangle associated proteins in Tauopathies including progressive supranuclear palsy (PSP), cortico-basal degeneration (CBD), agyrophilic grain disease (AGD), fronto-temporal dementia (FTD, frontotemporal dementia with Parkinsonism (FTDP17), Alzheimer's disease Picks disease; ataxin in Spinocerebellar ataxia copper/zinc super oxide dismutase in Amyotrophic lateral sclerosis and TDP-43 in Frontotemporal Lobar Degeneration and Amyotrophic Lateral Sclerosis. In another embodiment, the stimulated immune response may also be directed against amyloid-associated proteins (Liao et al., J. Biol. Chem. 2004), or other forms of amyloidoses comprising fibrillar proteins derived from at least one of the following precursor proteins SAA (Serum-Amyloid-Protein A), AL (k or l-light chains of Immunoglobulins), AH (gl Ig-heavy chains), ATTR (Transthyretin, Serum-Prealbumin), AApo-A-1 (Apolipoprotein A1), AApoA2 (Apolipoprotein A2), AGel (Gelsolin), ACys (Cystatin C), ALys (Lysozyme), AFib (Fibrinogen), Beta-amyloid (Amyloid precursor protein), Beta-amyloid2M (beta2-microglobulin), APrP (Prion protein), ACal (Procalcitonin), AIAPP (islet amyloid polypeptide); APro (Prolactin), AIns (Insulin); AMed (Lactadherin); Aker (Keratoepithelin); ALac (Lactoferrin), Abri (AbriPP), ADan (ADanPP); or AANP (Atrial natriuretical peptide), In another embodiment the present invention relates to a diagnostic composition comprising any one of the above described binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the binding molecules, in particular antibodies of the present invention may also be used in a method for the diagnosis of a disorder in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used.

Thus, the present invention relates to an in vitro immunoassay comprising the antibody of the invention.

The present invention also provides a pharmaceutical and diagnostic, respectively, pack or kit comprising one or more containers filled with one or more of the above described ingredients, in particular immunostimulant, binding molecule, antibody or binding fragment thereof, as defined hereinbefore, and optionally reagents for detection of neo-epitope binding and/or instructions for use. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents conventionally used in immuno or nucleic acid based diagnostic methods and/or instructions for use in appropriate diagnostic assays. The composition, i.e. kit of the present invention is of course particularly suitable for the diagnosis, prevention and treatment of a disorder which is accompanied with the presence of a disorder-associated protein as defined above, especially amyloidosis, and in particular applicable for the treatment of Alzheimer's disease (AD).

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease. Administration of the pharmaceutical composition may be performed by various ways including but not limited to intravenously, intramuscularly, subcutaneously, intraperitoneally, intranasally, parenterally or as an aerosol.

Furthermore, the term "subject" or "patient" refers to a mammal, preferably a human, in need of treatment for a condition, disorder or disease.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intra-muscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

Furthermore, whereas the present invention includes the now standard (though fortunately infrequent) procedure of drilling a small hole in the skull to administer a drug of the present invention, in a preferred aspect, the binding molecule, especially antibody or antibody based drug of the present invention can cross the blood-brain barrier, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.1 mg per kilogram of body weight to 10 mg per kilogram of body weight (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg per kilogram of body weight units once or twice weekly. If the regimen is a continuous infusion, it should also be in the range of 1 µg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition. Furthermore, the pharmaceutical composition may also be formulated as a vaccine. It may also be a pharmaceutical composition of the invention comprising an anti-Abeta antibody for passive immunization.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Preferably, the therapeutic agent in the composition is present in an amount sufficient to measurably improve normal behavior and/or cognitive properties in case of Alzheimer's disease.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness are given in Berks, TIBTECH 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech.

Animals

APPsweArc transgenic mice were generated and breed as previously described (Knobloch et al., 2006). Mice were kept under standard housing conditions and had free access to food and water. The treatment groups were balanced for age (14-15 months at start), gender and littermates (genetic background).

Treatment and Treatment Groups

Three groups of APPsweArc transgenic mice and two groups of wild type littermates were analyzed. The first group of APPsweArc mice were treated biweekly i.p. with 50 μg CPG 1826 (Coley Pharmaceutical Group Inc.) diluted in sterile endotoxin free PBS with a constant injection volume of 100 μl per mice. A second group of APPsweArc mice was treated once weekly i.p. with 10 μg CPG 1826. A third group of APPsweArc mice was injected biweekly i.p. with 100 μl of PBS. Two groups of wild type mice were either treated biweekly i.p. with 50 μg CPG 1826 or were left untreated. Animals were observed on a regular basis for any signs of illness and/or distress. CPG 1826 or PBS were administered for a total of 20 weeks, starting with an age between 14 and 15 months.

Group 1: APPsweArc mice; 50 μg CPG 1826 2× weekly i.p. (n=9)

Group 2: APPsweArc mice; 10 μg CPG 1826 1× weekly i.p. (n=8)

Group 3: APPsweArc mice; PBS 2× weekly i.p. (n=10)

Group 4: wt littermates; 50 μg CPG 1826 2× weekly i.p. (n=8)

Group 5: wt littermates, untreated (n=6)

Y-Maze Behavior Testing

Mice were adapted to a reversed light cycle at least a week before the experiment. Mice were placed into the Y-Maze (40 cm arm length) and explored for 5 min. Movements were recorded with a camera and the EthoVision software, arm entries were recorded manually. The percent alternation was calculated as the ratio of actual to possible alternations (defined as the total number of arm entries−2)×100%.

Radial Arm Water Maze Behavior Testing

One week after the Y-Maze mice were tested in the radial arm water maze (RAWM) according to Alamed et al. (2006). RAWM was conducted for four consecutive days. On day 1, mice were presented for the first 12 trials with alternating visible and hidden platform. On day 2 and 3 mice were trained with hidden platform only. On day 1 to 3 the position of the platform remained the same. On day 4 the location of the platform was changed and mice had to find the new location of the platform. Each trial lasted a maximum of 60 sec, the inter trial interval was approx. 10 min. Each mouse performed a total of 15 trials per day.

Analysis of Brain Levels of Aβ40 and Aβ42

For Phosphate buffered saline (PBS) brain homogenates, frozen hemibrains (excluding brainstem, cerebellum and optic lobes) were homogenized with a dounce homogenizer in 5 volumes of TBS with a protease inhibitor cocktail (Roche Applied Science, Indianapolis, Ind.). The samples were centrifuged at 175,000 g for 30 minutes at 4° C. The supernatant (PBS-soluble homogenate) was collected and stored at −80° C. The pellets were resuspended in the same volume of PBS-T (TBS/1% triton X-100 plus protease inhibitor cocktail) buffer, sonicated for 5 mM in 4° C. water bath, homogenized, and centrifuged at 175,000 g for 30 min at 4° C. The supernatant (PBS-T-soluble homogenate), containing membrane-bound Aβ, was collected and stored at −80° C. The pellets were extracted a third time as previously described (Johnson-Wood et al., 1997) using ice cold guanidine buffer (5 M guanidine-HCl/50 mM Tris, pH 8.0) (herein referred to as PBS-insoluble or guanidine homogenate). Aβ1-40 (Aβ40) and Aβ1-42 (Aβ42) levels were determined in PBS, PBS-T and guanidine brain homogenates. Concentrations of Aβ40 and Aβ42 were determined by ELISA using the β AMYLOID [1-40] and β AMYLOID [1-42] ELISA kits (Invitrogen, USA) according to manufacturer's instructions.

Histology and Plaque Load Analysis

Mice selected for histology were anesthetized (10 ml/g body weight ketamin/xylaxine) and perfused transcardially with PBS. One brain hemisphere was immediately frozen on dry-ice for further biochemical analysis. The other hemisphere was fixed over night in 4% paraformaldehyde. 30 μm floating coronal sections were prepared using a sliding microtome. Congo Red Staining for compact plaques was performed according to Wilcock et al. (2006). Antibody staining for both compact and diffuse plaques was performed with α-Aβ rabbit polyclonal antibody (Zymed, USA). Quantification of Congo Red and Aβ staining was done using the ImageProPlus software (MediaCybernetics, Germany). 2 series of 8 sections per animal were used for quantification.

Anti-Abeta Autoantibody ELISA

Half-area 96 well plates (Corning) were coated over night with 1 μg/ml of fibrillar Aβ42 or Aβ40 in coating buffer (carbonate buffer, pH 9.6). 1:20 or 1:100 dilutions of mouse plasma were incubated for 1.5 hours followed by detection with standard HRP-coupled anti-mouse secondary antibody (Jackson Laboratories, USA).

Example 1

Induction of Elevated Titers of Anti-Beta-Amyloid-Plaque Antibodies Concomitant with Reduced Plaque Load in APP Transgenic Mice The hypothesis underlying the present invention is confirmed by applying CpG-motifs or SIMRA compounds to immunocompetent amyloid precursor protein transgenic mice with low baseline-levels of auto-antibodies against the human Abeta peptide. In a preferred embodiment of the present invention, the transgenic animal is a mouse harboring a transgene encoding amyloid precursor protein (APP) consisting of the arctic mutation (G693G) and the Swedish mutation (KM670/671NL), under the control of the prion protein promoter (PrP) named arcAbeta mouse (Knobloch et al., Neurobiol. Aging July 28 (2006). Aged arcAbeta mice are treated with a single or multiple subcutaneous injections of 0.2 to 20 mg/kg body weight of completely phosphorothioate-modified CpG-oligodeoxyribonucleotide 1826 which is assumed to be a kind of equivalent to the human TLR-9 agonist CpG 7909 (called ProMune™ (Coley Pharmaceuticals)) or the control nonstimulatory oligodeoxyribonucleotide 1982; for nucleotide sequences see Milas et al., Cancer Research 64 (2004), 5074-5077 and the references cited above. Serum samples are analyzed for anti-beta-amyloid antibodies by ELISA and TAPIR assay; see supra. Antibody titers are determined by serial dilution of the sera and increased serum titers of beta-amyloid specific antibodies can be detected in the CpG-oligodeoxyribonucleotide 1826 treated animals compared to the control group treated with the nonstimulatory oligodeoxyribonucleotide 1982. Three to six month after initiation of treatment, mice are anesthetized (10 µl/g bw ketamin/xylaxine) and perfused transcardially with PBS. The brains are fixed in 4% paraformaldehyde and embedded in paraffin. Sum sagittal sections are cut with a Leica RM 2135 microtome (Bannockburn, Ill.). For immunohistochemistry, slices are dewaxed, blocked with 4% BSA, 5% goat serum and 5% horse serum in PBS for 1 h at RT. For the detection of brain beta-amyloid plaques, 6E10 antibody (Signet) at 1:500 dilution is incubated overnight at 4° C. followed by incubation with secondary fluorophore coupled antibodies at RT for 2 h. 3 sections per brain, ~75 µm apart are used for the analysis. 2 images per section are taken at 10× magnification using an inverted microscope (Leica DMIRE2) and quantitative analysis of cortical β-amyloid plaque load is performed using the ImageJ software (http://rsb.info.nih.gov/ij/).

Example 2

CpG Treatment Improves Behavior in Transgenic Mouse Models of Alzheimer's Disease In the Y-maze, a reduced number of arm entries was observed for the PBS treated transgenic APPsweArc mice compared to both groups of wild type littermates analyzed (FIG. 1a). Treatment with either 10 or 50 µg of CpG resulted in an increased number of arm entries indicating a higher level of exploratory activity. Similarly, the percentage of alternations was reduced in PBS treated APPsweArc mice compared to both wild type groups indicating impaired working memory (FIG. 1b). In contrast, APPsweArc mice treated with either dose of CpG performed similar to wild type mice, suggesting that the CpG treatment improved cognitive function.

Figure 2:
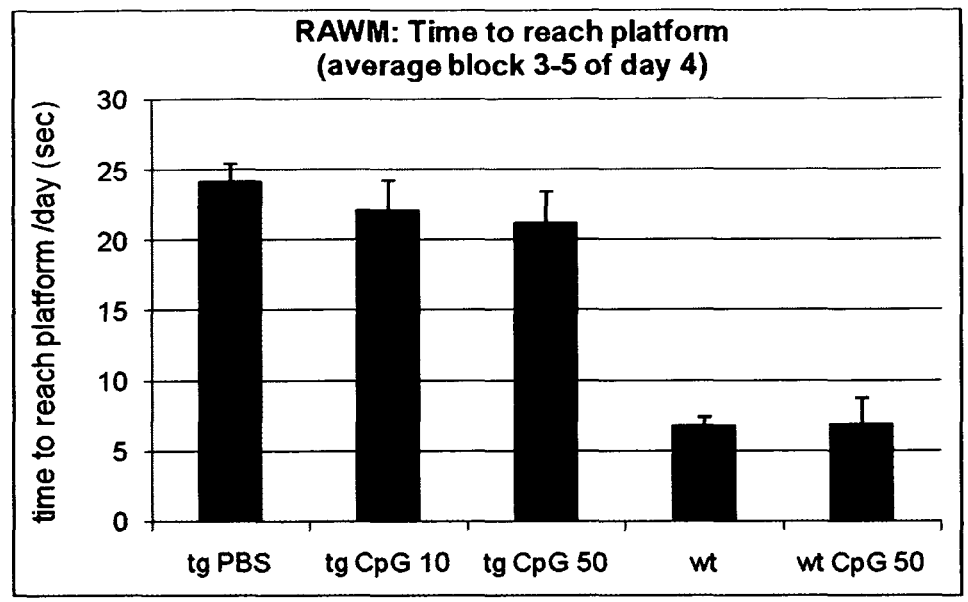
FIG. 2: Average time(A) and errors (B) to reach the platform of block 3-5 of day 4. CpG treatment of APPsweArc is associated with a trend for a dose-dependent improvement in learning performance.
Figure 2:
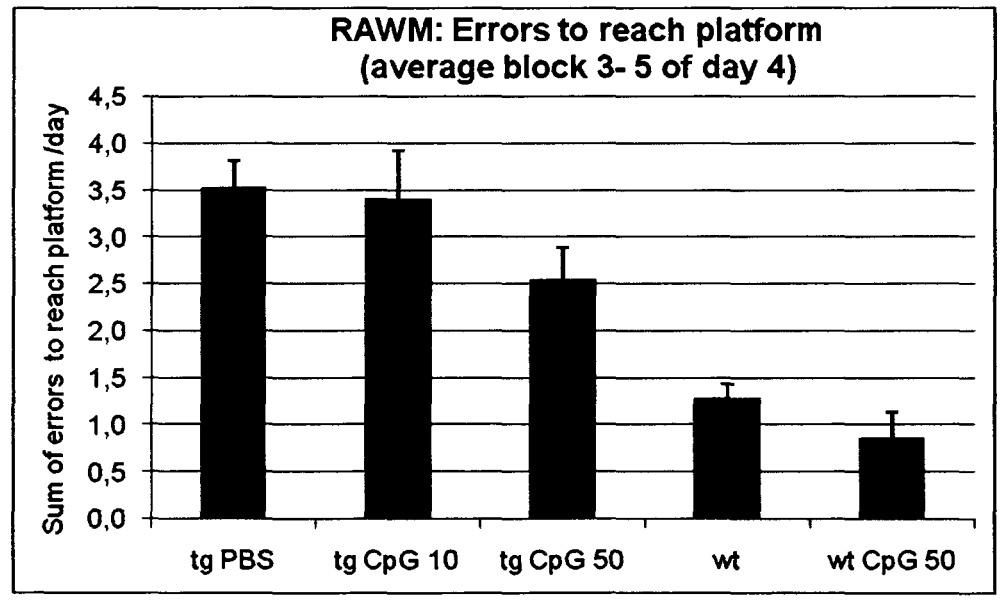

In the RAWM experiments average time and errors to reach the platform was analyzed for blocks 3-5 of day 4. PBS-treated APPsweArc mice exhibit increased time (FIG. 2a) and error rate (FIG. 2b), respectively, compared to both wt groups. Treatment with either 10 µg or 50 µg of CpG is associated with a trend for a dose-dependent improvement in the time needed to locate the platform as well as the frequency of errors. This suggests that CpG treatment can improve learning performance in the APPsweArc transgenic mouse models of Alzheimer's disease.

Example 3

Figure 3:
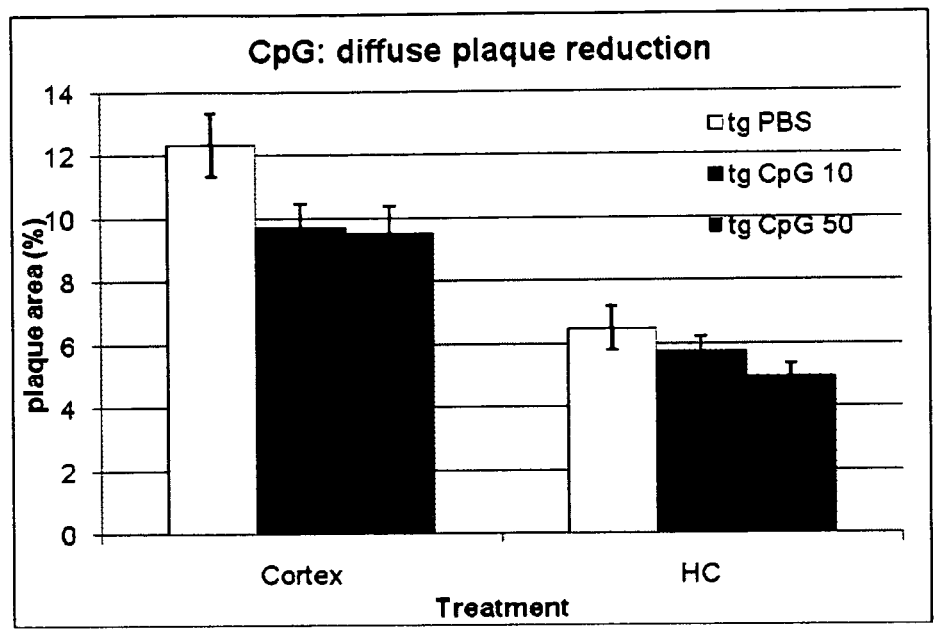
FIG. 3: Total Aβ plaque load (Zymed pan-Aβ) and compact congophilic amyloid deposits (Congo Red) in cortex and hippocampus (HC) of APPsweArc mice. Reduced levels of total and compact Aβ plaque pathology were observed upon chronic treatment with 10 µg or 50 µg of CpG compared to the PBS control animals.
Figure 3:
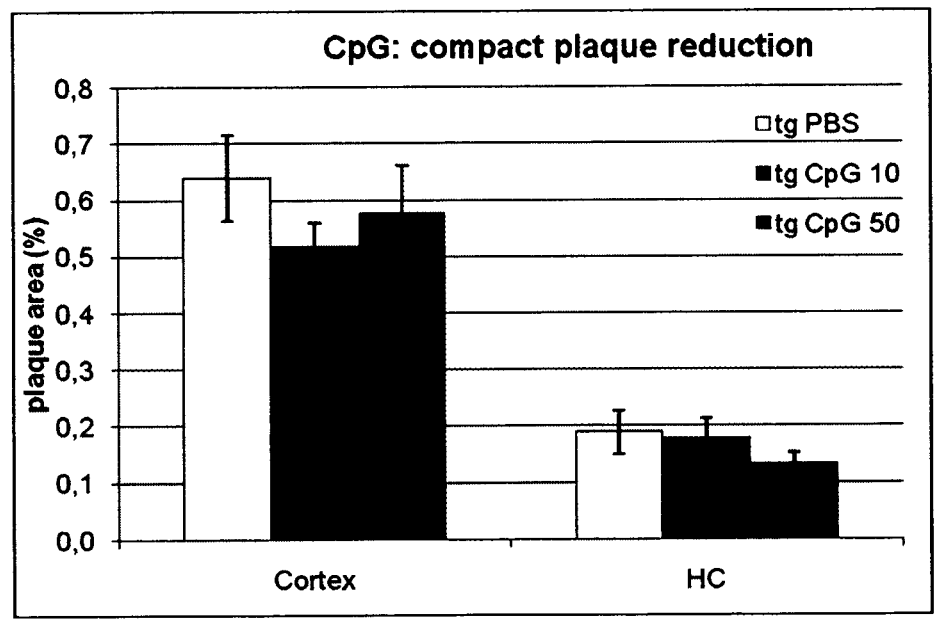

CpG Treatment Reduces Total Brain Aβ Plaque Load and Compact Congophilic Amyloid Deposits Total Aβ immunohistochemistry using a polyclonal anti-Aβ antibody revealed extensive deposition of Aβ plaques in the cortex and hippocampus (FIG. 3a) of PBS treated APPsweArc transgenic mice. Treatment with either 10 µg or 50 µg CpG was associated with a clear trend towards a dose dependent reduction in total Aβ plaque load. A similar reduction was observed for compact congophilic amyloid deposits as revealed by Congo red staining indicating that chronic treatment with CpG desoxynucleotides can ameliorate amyloid plaque pathology.

Example 4

CpG Treatment Reduces Brain Soluble and Insoluble Aβ

Figure 4:
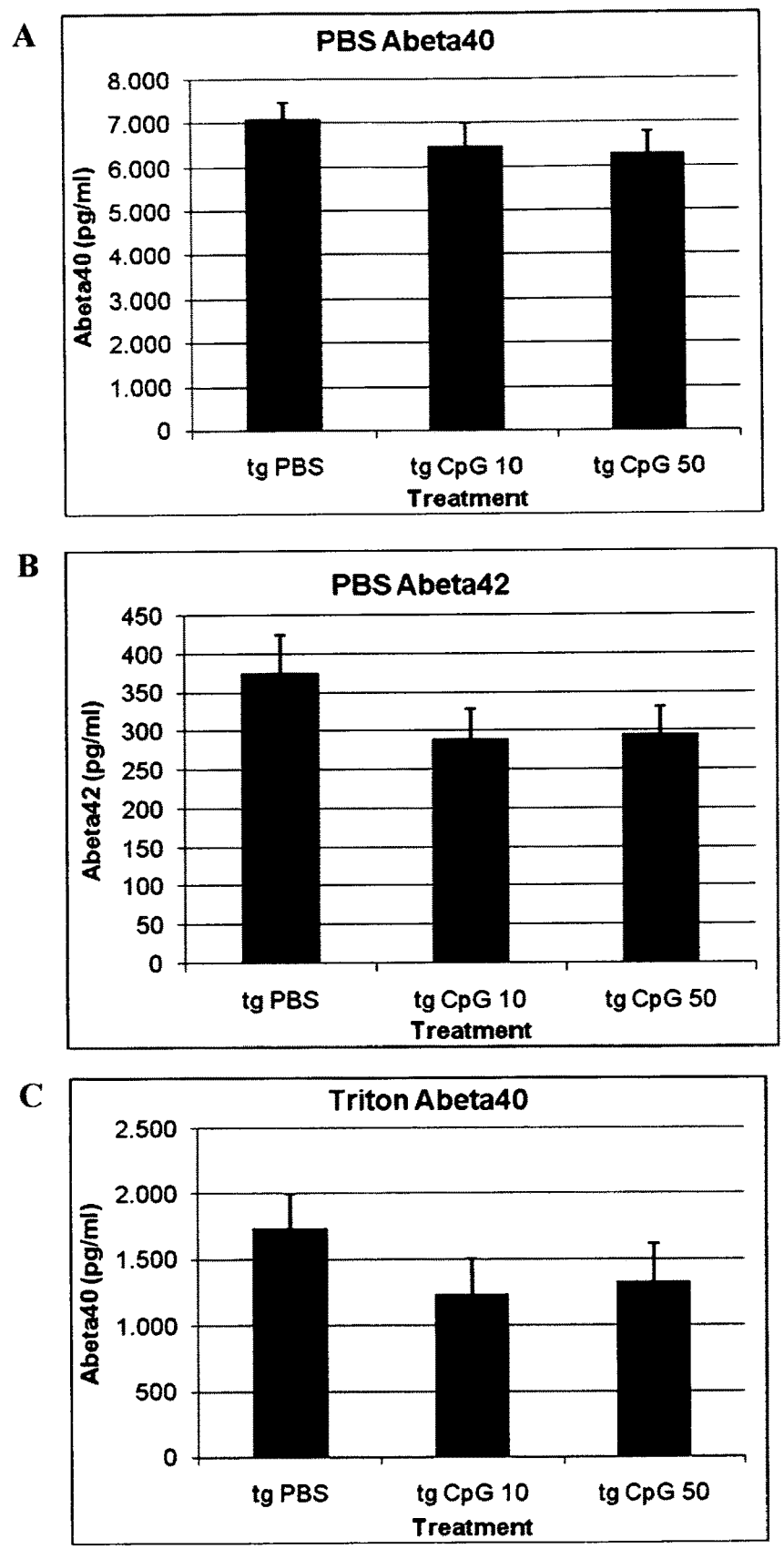
FIG. 4: Levels of soluble brain Aβ40 and Aβ42 in PBS and TritonX-100 brain extracts. Both CpG-treatment regimens decrease the brain levels of Aβ40 and Aβ42. Levels of TritonX-100 Aβ42 were below the detection limit of the ELISA and were therefore not analyzed.
Figure 5:
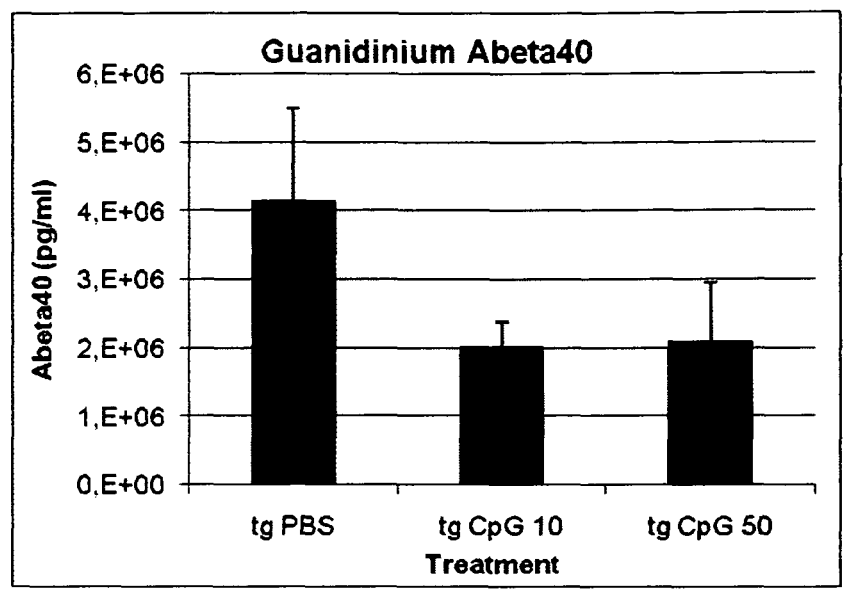
FIG. 5: Levels of insoluble brain Aβ40 and Aβ42 in Guanidine brain extracts. Both CpG treatment regimens decrease the brain levels of insoluble Aβ compared to the control group (PBS) by up to 50%.
Figure 5:
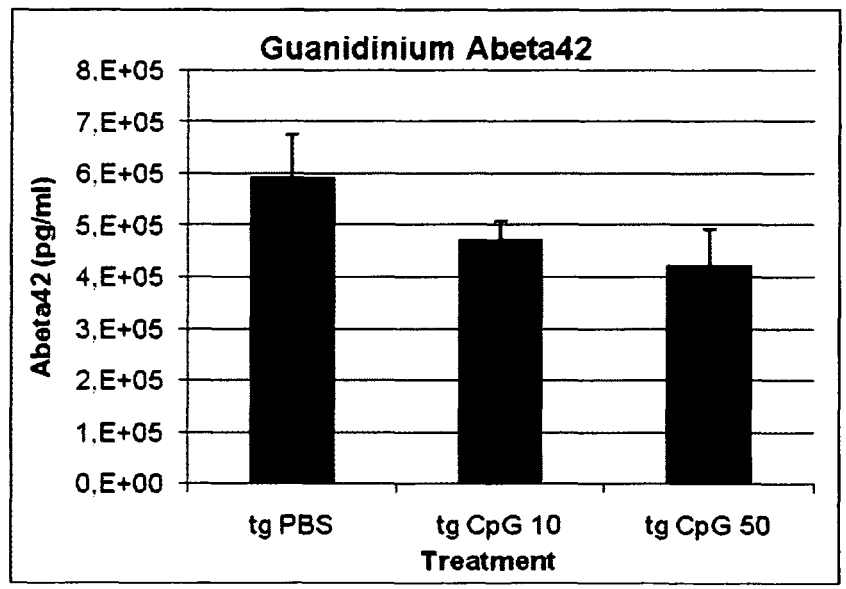
Figure 6:
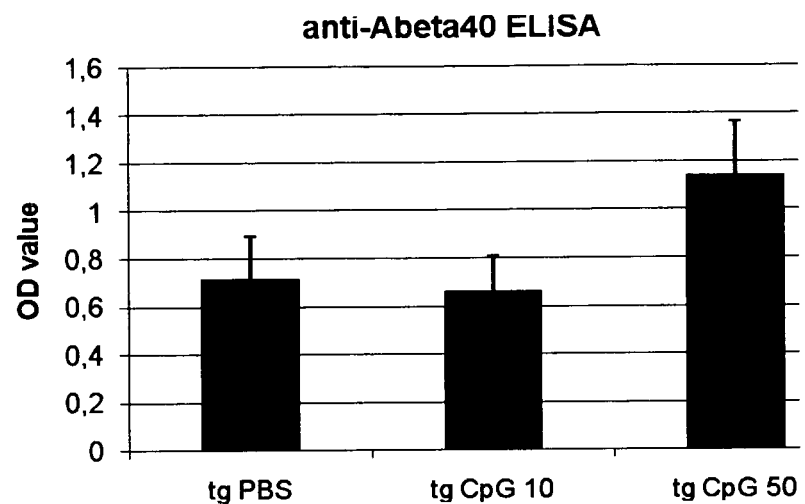
FIG. 6: Terminal bleed Aβ40 and Aβ42 binding antibody levels are increased in APPsweArc mice upon CpG treatment.
Figure 6:
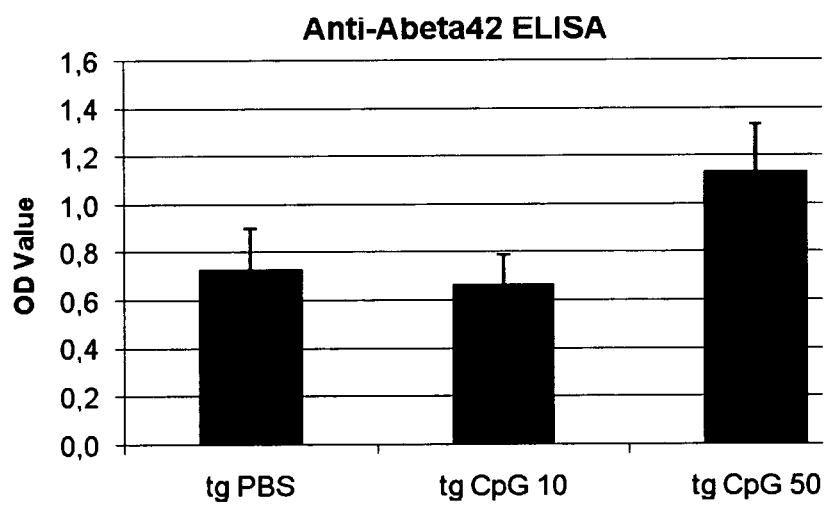

To assess the effects of CpG treatment on soluble and insoluble brain levels of Aβ40 and Aβ42, brains of APPsweArc mice were sequentially extracted in PBS, PBS/Triton X-100 and Guanidine and Aβ levels in each fraction were analyzed by sandwich ELISA. Upon chronic CpG treatment modest reductions in soluble brain Aβ40 and Aβ42 levels were observed in the in PBS (FIG. 4a, b) and PBS/Triton X-100 fractions (FIG. 4c). Cerebral insoluble levels of Aβ40 and Aβ42 as measured by guanidine extraction were strongly reduced by up to 50% in both CpG treatment groups compared to PBS treated transgenic animals (FIG. 5). Due to a high variability and small group size, the observed changes did not reach significance. These data are in agreement with the observed effects on Aβ plaque load and indicate that CpG treatment can ameliorate the pathologic brain accumulation and deposition of Aβ in transgenic Alzheimer's disease model mice.

Example 4

CpG Treatment Enhances Plasma Antibodies Directed Against Fibrillar Abeta

The plasma titers of autoantibodies directed against beta-amyloid fibrils were measured by ELISA analysis of terminal bleed plasma. A strong increase in circulating antibodies to beta-amyloid fibrils was detected in the 50 µg CpG treatment group suggesting that elevated levels of beta-amyloid autoantibodies were induced and still detectable at the end of the treatment paradigm. No difference was detected between total IgG and IgM levels between different groups. CpG treatment further resulted in increased plasma levels of Aβ40 and Aβ42 suggesting a shift of Abeta from the brain towards peripheral compartments.

Summary

In accordance with the present invention it was surprisingly found that and as the basis of this invention it could be shown, that APP transgenic mice displayed significantly elevated titers of antibodies directed against beta-amyloid-plaques and significantly reduced brain beta-amyloid plaque load following treatment with the CpG-oligodeoxyribonucleotide but not the control non-CpG containing oligo-nucleotide or PBS. In accordance with the present invention it is believed, though not intended to be bound by theory, that preexisting antibodies preferably reactive with non-neo-epitopes of beta-amyloid are successfully suppressed by phenomena of tolerance, while B-cells directed against neo-epitopes present in beta-amyloid-plaques get stimulated, thus not substantially inducing an undesired type of autoimmune disease. In summary, a novel approach for treating conditions associated with amyloidosis including Alzheimer's disease as well as other diseases and disorders that are caused by the accumulation of abnormal protein structures and peptide aggregation, in particular neurodegenerative diseases has been established.

LITERATURE

Alamed, J., et al., Two-day radial-arm water maze learning and memory task; robust resolution of amyloid-related memory deficits in transgenic mice. Nat Protoc, 2006. 1(4): p. 1671-9.

Bernasconi, N. L., Traggiai, E., Lanzavecchia, A. Maintenance of serological memory by polyclonal activation of human memory B-cells. Science 2002; 298: 2199-2202.

Brettschneider, S., Morgenthaler, N. G., Teipel, S. J., Fischer-Schulz, C., Burger, K., Dodel, R., Moller, H. J., Bermann, A., Hampel, H. Decreased serum amyloid beta (1-42) autoantibody levels in Alzheimer's disease, determined by a newly developed immuno-precipitation assay with radiolabeled amyloid beta (1-42) peptide Biol. Psychiatry. 57 (2005) 813-816.

Buxbaum, Curr Opin Rheumatol 2003; 16: 67-75

Davis, H., Schorr, J., Krieg, A. M., Use of Nucleic Acids containing unmethylated CpG dinucleotide as an adjuvant. (2002) U.S. Pat. No. 6,406,705

Davis, Heather L., Risini Weeranta, Thomas J. Waldschmidt, Lorraine Tygrett, Joachim Schorr and Arthur M. Krieg CpG DNA Is a Potent Enhancer of Specific Immunity in Mice Immunized with Recombinant Hepatitis B Surface Antigen, The Journal of Immunology, 1998, 160: 870-876

Ertesvag, A., Aasheim, H. C., Naderi, S., Blomhoff, H. K. Vitamin A potentiates CpG-mediated memory B-cell proliferation and differentation: involvement of early activation of p38MAPK. Blood. 2007; 109, 9: 3865-3872.

Hartmann, G. Krieg, A. M. Mechanism and function of a newly identified CpG DNA motif in human primary B-cells J Immunology 2000, 164: 944-953.

Hartmann, G., Weeratna, R. D., Ballas, Z. K. et al. Delineation of a CpG Phosphorothioate Oligodeoxynucleotide for Activating Primate Immune Responses In Vitro and In Vivo. The Journal of Immunology (2000), 164, 1617-1624.

Hock C, Konietzko U, Streffer J R, Tracy J, Signorell A, Muller-Tillmanns B, Lemke U, Henke K, Moritz E, Garcia E, Wollmer M A, Umbricht D, de Quervain D J, Hofmann M, Maddalena A, Papassotiropoulos A, Nitsch R M. Antibodies against beta-amyloid slow cognitive decline in Alzheimer's disease. Neuron. 2003 May 22; 38(4):547-54.

Iribarren, P., Chen, K., Hu, J., Gong, W., Cho, E. H., Lockett, S., Uranchimeg, B., Wang, J. M. CpG-containing oligodeoxynucleotide promotes microglial cell uptake of amyloid b 1-42 peptide by up-regulating the expression of the G-protein-coupled receptor mFPR2. The FASEB Journal express article (2005) October 11.

Johnson-Wood, K., et al., Amyloid precursor protein processing and A beta42 deposition in a transgenic mouse model of Alzheimer disease. Proc Natl Acad Sci USA, 1997. 94:1550-1555.

Knobloch M, Konietzko U, Krebs D C, Nitsch R M. Intracellular Abeta and cognitive deficits precede beta-amyloid deposition in transgenic arcAbeta mice. Neurobiol Aging. 2007 September; 28(9):1297-306.

Krieg, A. M., Schetter, C., Vollmer, J. Immunostimulatory nucleic Acids United States Patent Appl. (2007) 20070066554 A1

Küppers, R. B cells under influence: Transformation of B cells by Epstein-Barr Virus Nature Review (2003), 3, 801.

Lanzavecchia and Sallusto, Curr Opin Immunol. 2007 June; 19(3):268-74.

Lee et al., 2005 Ann Neurol 2005; 58:430-35

Liao L, Cheng D, Wang J, Duong D M, Losik T G, Gearing M, Rees H D, Lah J J, Levey A I, Peng J. Proteomic characterization of postmortem amyloid plaques isolated by laser capture microdissection. J Biol Chem. 2004 Aug. 27; 279(35):37061-8.

Moir, R. D., Tseitlin, K. A., Soscia, S., Hyman, B. T., Irizarry, M. C., Tanzi, R. E., Auoantibodies to redox-modified oligomeric Amyloid beta are attenuated in the plasma of Alzheimer's disease patients. J. Biol. Chem. 280 (2005) 17458-17463.

Orgogozo J M, Gilman S, Dartigues J F, Laurent B, Puel M, Kirby L C, Jouanny P, Dubois B, Eisner L, Flitman S, Michel B F, Boada M, Frank A, Hock C. Subacute meningoencephalitis in a subset of patients with AD after Abeta42 immunization. Neurology. 2003 Jul. 8; 61(1):46-54.

Pfeifer M, Boncristiano S, Bondolfi L, Stalder A, Deller T, Staufenbiel M, Mathews P M, Jucker M. Cerebral hemorrhage after passive anti-Abeta immunotherapy. Science. 2002 Nov. 15; 298(5597):1379.

Skovronsky D M, Lee V M-Y, Trojanowski J Q: Neurodegenerative diseases: new concepts of pathogenesis and their therapeutic implications. Annu Rev Pathol Mech Dis 2006, 1:151-170

Song et al., Serum anti-amyloid-beta antibodies and Alzheimer's disease in elderly Korean patients J Int Med Res. 2007 May-June; 35(3):301-6)

Tao Lan, Ekambar R. Kandimalla, Dong Yu, Lakshmi Bhagat, Yukui Li, Daqing Wang, FuGang Zhu, Jimmy X. Tang, Mallikarjuna R. Putta, YanPing Cong, Anthony F. Trombino, Tim Sullivan, and Sudhir Agrawal "Stabilized immune modulatory RNA compounds as agonists of Toll-like receptors 7 and 8" PNAS U.S.A. 104: 13750-13755, 2007

Traggiai, E., Becker, S., Subbaro, K., Kolesnikova, L., Uematsu, Y., Gismondo, M. R., Murphy, B. R., Rappuoli, R., Lanzavecchia, A. An efficient method to make human monoclonal antibodies from memory B cells: potent neutralization of SARS coronavirus. Nature Medicine (2004) 10,8, 871-75.

Weksler, M. E., Relkin, N., Turkenich, R., LaRusse, S., Zhou, L., Szabo, P., Patients with Alzheimer disease have lower levels of serum anti-amyloid peptide antibodies than healthy elderly individuals. Exp. Gerontol. 37 (2002) 943-948.

Wilcock, D. M., M. N. Gordon, and D. Morgan, Quantification of cerebral amyloid angiopathy and parenchymal amyloid plaques with Congo red histochemical stain. Nat Protoc, 2006. 1(3): p. 1591-5

The invention claimed is:

1. A method of treating Alzheimer's Disease pathology in a subject, which method comprises:
   administering, to the subject twice weekly for 3 to 5 months, an oligonucleotide or modified oligonucleotide containing at least one unmethylated B-class CpG dinucleotide motif at a dosage in a range of 0.2 mg to 20 mg per kilogram body weight of the selected subject, wherein said administering is effective to reduce (i) total and compact Aβ plaque pathology, (ii) soluble brain Aβ40 and Aβ42, and (iii) insoluble brain Aβ40 and Aβ42 as compared to when the administering step is not carried out, thereby treating Alzheimer's Disease pathology.

2. The method of claim 1, wherein the oligonucleotide is formulated as a pharmaceutical composition, optionally together with a pharmaceutically acceptable carrier.

3. The method of claim 1, wherein the oligonucleotide is administered at a subclinical stage of the disease.

4. The method of claim 2, wherein said pharmaceutical composition comprises at least one non-nucleic acid adjuvant capable of creating a depo effect.

5. The method of claim 4, wherein the adjuvant is selected from the group consisting of alum, emulsion based formulations, mineral oil, non-mineral oil, water-in-oil emulsions, water-in-oil-in-water emulsions, and the Seppic ISA series of Montanide adjuvants.

6. The method of claim 4, wherein the adjuvant comprises an immune stimulating adjuvant.

7. The method of claim 4, wherein the adjuvant comprises vitamin A.

8. The method of claim 4, wherein the adjuvant comprises a compound selected from the group consisting of saponins, PCPP polymer, derivatives of lipopolysaccharides, Monophosphoryl A (MPL), muramyldipeptide (MDP), threonyl-muramyl dipeptide (t-MDP), Leishmania elongation factor, and glatiramer acetate.

9. The method of claim 4, wherein the adjuvant that creates a depo effect and stimulates the immune system is selected from the group consisting of Immune Stimulating Complexes (ISCOMS), Adjuvant System 2 (AS2), Adjuvant System 4 (AS4), non-ionic block copolymers, and Syntex adjuvant formulation (SAF).

10. The method of claim 1, wherein said administering is performed intravenously, intramuscularly, subcutaneously, intraperitoneally, intranasally, parenterally, or as an aerosol.

11. The method of claim 1, wherein the administration is carried out for 3 months.

12. The method of claim 1, wherein the administration is carried out for 4 months.

13. The method of claim 1, wherein the administration is carried out for 5 months.

14. The method of claim 1, wherein the oligonucleotide or modified oligonucleotide contains at least two unmethylated B-class CpG dinucleotide motifs.

15. The method of claim 1, wherein the oligonucleotide or modified oligonucleotide contains two unmethylated B-class CpG dinucleotide motifs.

16. The method of claim 1, wherein said administering is carried out without co-administration of exogenous immunogen.

17. The method of claim 1, wherein the subject has a mutation in the beta-amyloid precursor protein (APP) gene.

18. The method of claim 1, wherein the subject has familial Alzheimer's Disease.

19. The method of claim 1, wherein said administering is effective to induce an autoantibody response.

* * * * *